United States Patent
Torii et al.

(10) Patent No.: US 11,043,287 B2
(45) Date of Patent: Jun. 22, 2021

(54) INFORMATION PROCESSING APPARATUS AND INFORMATION PROCESSING METHOD

(71) Applicant: TEIJIN LIMITED, Osaka (JP)

(72) Inventors: Kentaro Torii, Tokyo (JP); Satoshi Aida, Tokyo (JP); Tetsuro Chino, Tokyo (JP); Mitsuyoshi Tachimori, Tokyo (JP); Takanori Yamamoto, Tokyo (JP)

(73) Assignee: TEIJIN LIMITED, Osaka (JP)

( * ) Notice: Subject to any disclaimer, the term of this patent is extended or adjusted under 35 U.S.C. 154(b) by 17 days.

(21) Appl. No.: 15/120,105

(22) PCT Filed: Feb. 18, 2015

(86) PCT No.: PCT/JP2015/054392
§ 371 (c)(1),
(2) Date: Aug. 18, 2016

(87) PCT Pub. No.: WO2015/125810
PCT Pub. Date: Aug. 27, 2015

(65) Prior Publication Data
US 2017/0063737 A1 Mar. 2, 2017

(30) Foreign Application Priority Data
Feb. 19, 2014 (JP) .............................. JP2014-029869

(51) Int. Cl.
*G16H 10/60* (2018.01)
*G16H 40/20* (2018.01)
(Continued)

(52) U.S. Cl.
CPC ........... *G16H 10/60* (2018.01); *G06F 16/338* (2019.01); *G16H 40/20* (2018.01); *H04L 51/04* (2013.01)

(58) Field of Classification Search
CPC ........ G16H 40/20; G16H 10/60; G16H 15/00; G16H 20/30; G16H 20/70; G16H 40/67;
(Continued)

(56) References Cited

U.S. PATENT DOCUMENTS 8,311,848 B2 * 11/2012 Subash .................. G06Q 10/10 705/2
8,589,778 B2 * 11/2013 Boyle .................... G06Q 10/10 715/201

(Continued)

FOREIGN PATENT DOCUMENTS

EP 2284747 A1 2/2011
JP 2003-036261 A 2/2003
(Continued)

OTHER PUBLICATIONS

Anonymous. "Automated System to Log and Process Medical Data for Caretakers of Chronic Care Patients." IP.com Prior Art Database. Jan. 16, 2009 (Year: 2009).*

(Continued)

*Primary Examiner* — Vivek Srivastava
*Assistant Examiner* — William C McBeth
(74) *Attorney, Agent, or Firm* — Marshall, Gerstein & Borun LLP

(57) ABSTRACT

An information processing apparatus includes: a first storage to store correspondence data that includes a plurality of mental and physical states and keywords related to each of the states; a second storage to store messages representing contents tweeted for an observed target by a plurality of observers; and a data processor to detect keywords related to each of the states from the messages based on the correspondence data and create presentation information which includes information data arranged correspondingly to each of the states wherein the information data is arranged for (Continued)

each of the messages including the keywords related to the corresponding state and includes the keyword detected from the each of the messages.

20 Claims, 14 Drawing Sheets

(51) Int. Cl.
*G06F 16/338* (2019.01)
*H04L 12/58* (2006.01)

(58) Field of Classification Search
CPC ...... G16H 50/70; G16H 80/00; G06F 19/322; G06F 19/327; G06F 17/30696; G06F 16/338; G06F 19/32; G06Q 50/22; H04L 51/04; Y02A 90/24
USPC .......................................... 709/206; 715/259
See application file for complete search history.

(56) References Cited

U.S. PATENT DOCUMENTS

| | | | | |
|---|---|---|---|---|
| 8,630,842 | B2* | 1/2014 | Sorkey | G16H 10/60 704/9 |
| 9,420,970 | B2* | 8/2016 | Dagum | G06F 19/3418 |
| 9,521,234 | B2* | 12/2016 | Aizawa | G10L 15/20 |
| 9,824,185 | B2* | 11/2017 | Douglass | G06F 17/30011 |
| 9,875,081 | B2* | 1/2018 | Meyers | G06F 3/167 |
| 2002/0046062 | A1* | 4/2002 | Kameda | G16H 10/60 705/3 |
| 2005/0028085 | A1* | 2/2005 | Irwin | H04M 3/4938 715/234 |
| 2005/0171762 | A1* | 8/2005 | Ryan | G16H 15/00 704/200 |
| 2007/0061361 | A1* | 3/2007 | Tanaka | A61B 5/02055 |
| 2008/0189633 | A1 | 8/2008 | Boyle et al. | |
| 2009/0024411 | A1* | 1/2009 | Albro | G06Q 10/10 705/2 |
| 2009/0112623 | A1* | 4/2009 | Schoenberg | G06F 19/328 705/2 |
| 2010/0114597 | A1* | 5/2010 | Shreiber | G06F 19/321 705/2 |
| 2010/0138231 | A1* | 6/2010 | Linthicum | G16H 15/00 705/2 |
| 2011/0010195 | A1* | 1/2011 | Cohn | G16H 10/60 705/3 |
| 2011/0029325 | A1* | 2/2011 | Georgiev | G06Q 10/06 705/3 |
| 2011/0112835 | A1* | 5/2011 | Shinnishi | G06F 40/268 704/235 |
| 2011/0190701 | A1* | 8/2011 | Remde | G06F 19/3456 604/131 |
| 2012/0004902 | A1* | 1/2012 | Sorkey | G16H 10/60 704/9 |
| 2012/0158432 | A1* | 6/2012 | Jain | G16H 15/00 705/3 |
| 2012/0166226 | A1* | 6/2012 | Lee | G06Q 50/24 705/3 |
| 2013/0132110 | A1* | 5/2013 | Nagaoka | G16H 20/70 705/2 |
| 2014/0019468 | A1* | 1/2014 | Federoff | G06Q 50/01 707/758 |
| 2014/0228010 | A1* | 8/2014 | Barbulescu | H04W 4/029 455/414.4 |
| 2014/0229229 | A1* | 8/2014 | Hirate | G06Q 10/00 705/7.29 |
| 2014/0244285 | A1* | 8/2014 | Hinkle | G16H 10/60 705/2 |
| 2014/0324424 | A1* | 10/2014 | Kim | G10L 15/22 704/235 |
| 2015/0149207 | A1* | 5/2015 | O'Keefe | G06F 19/3456 705/3 |
| 2015/0201246 | A1* | 7/2015 | Son | G10L 15/22 725/53 |
| 2015/0216413 | A1* | 8/2015 | Soyao | G16H 20/60 709/204 |
| 2016/0117469 | A1* | 4/2016 | Tesanovic | G16H 50/70 705/3 |
| 2016/0127280 | A1* | 5/2016 | Nair | H04L 51/04 709/206 |
| 2016/0180023 | A1* | 6/2016 | Wilson | G16H 10/60 705/3 |
| 2017/0316180 | A1* | 11/2017 | Takeda | G06Q 10/04 |

FOREIGN PATENT DOCUMENTS

| | | |
|---|---|---|
| JP | 2006-215675 A | 8/2006 |
| JP | 2012-226449 A | 11/2012 |
| JP | 5414865 B1 | 2/2014 |

OTHER PUBLICATIONS

Kumi Ikegami, "Innovation of Medical and Nursing Care Services by Utilizing 'Mutterings'," Japan Science and Technology Agency, pp. 3-7 Dec. 2, 2013.

European patent application No. 15751732.7, Extended European Search Report, dated Oct. 2, 2017.

Uchihira et al., Collaboration management by smart voice messaging for physical and adaptive intelligent services, pp. 251-258, 2013 Proceedings of PICMET '13: Technology Management for Emerging Technologies (2013).

International Search Report and Written Opinion, corresponding to international application No. PCT/JP2015/054392, dated May 26, 2015.

International Preliminary Report on Patentability, corresponding to international application No. PCT/JP2015/054392, dated Aug. 23, 2016.

* cited by examiner

| STATE | KEYWORD |
|---|---|
| COGNITION | WANDERING |
| COGNITION | UNREST |
| COGNITION | SPILLING FOOD |
| NUTRITION | SPILLING FOOD |
| MISSWALLOWING | SPILLING FOOD |
| MISSWALLOWING | CHOKED |
| TUMBLE/FALL | STUMBLE |
| TUMBLE/FALL | STAGGER |

FIG.2

| VOICE TWEET ID | OBSERVER ID | OBSERVED TARGET ID | DATE AND TIME WHEN TWEET OCCURRED | CONTENT OF VOICE TWEET | RELATED KEYWORD |
|---|---|---|---|---|---|
| 1058 | 1 | 2 | 2013/9/14 9:19 | TARGET IS SLIGHTLY INCLINING TO RIGHT. | INCLINE TO RIGHT |
| 1064 | 2 | 8 | 2013/11/14 9:21 | TARGET COMPLETED MEAL DOWNSTAIRS AND IS NOW UPSTAIRS. TARGET SAYS THAT HE/SHE WANTS TO RETURN TO ROOM QUICKLY, BUT OBSERVER CANNOT TAKE HIM/HER TO ROOM. OBSERVER ASKED TARGET TO WAIT. SEND HELPER. | WANT TO RETURN |
| 1067 | 6 | 4 | 2013/11/14 10:00 | TARGET IS STAYING UP LATER THAN USUAL TODAY. | STAY UP |
| 1071 | 1 | 4 | 2013/11/14 10:05 | TARGET SAYS THAT HE/SHE WANTS TO RETURN TO LIVING ROOM QUICKLY. SEND HELPER. | WANT TO RETURN, HELP |
| 1072 | 2 | 7 | 2013/11/14 10:06 | TARGET IS STAYING UP LATER THAN USUAL TODAY. | STAY UP |
| 1073 | 2 | 8 | 2013/8/14 10:08 | TARGET COMPLETED MEAL AND STARTED STANDING UP BY HIMSELF/HERSELF. OBSERVER ASSISTS TARGET IN WALKING. | MEAL, BY ONESELF, STAND UP, WALK, ASSISTANCE |
| 1074 | 6 | 7 | 2013/8/14 10:10 | BLOOD PRESSURE IS SLIGHTLY HIGHER THAN USUAL AND TARGET IS UNSTEADY ON HIS/HER FEET. BE CAREFUL THAT TARGET DOES NOT TUMBLE OR FALL. | BLOOD PRESSURE, FEET, TUMBLE, CAREFUL |
| 1076 | 8 | 4 | 2013/8/14 10:12 | TARGET WANTS TO GO TO TOILET AND STOOD UP. | TOILET, STAND |
| 1077 | 4 | 10 | 2013/8/14 10:14 | TARGET SITS DOWN WITHOUT CHECKING THINGS AT HIS/HER FEET. BE CAREFUL AT NEXT MEAL. | FEET, CHECK, SIT DOWN, MEAL, CAREFUL |
| 1078 | 4 | 6 | 2013/11/14 10:20 | TARGET SEEMS TO BE UNSURE ABOUT HOW TO EAT FISH. | FISH, UNSURE |
| 1079 | 4 | 6 | 2013/10/14 10:21 | TARGET WANDERED BY HIMSELF/HERSELF AFTER EVENING CARE. | BY ONESELF, WANDERING |
| 1080 | 2 | 9 | 2013/10/14 10:22 | TARGET STANDS UP DURING MEAL. BE CAREFUL. | MEAL, STAND |
| 1081 | 2 | 2 | 2013/11/14 10:26 | TARGET HAS POOR APPETITE. PRESCRIBE MEDICINE. | APPETITE |
| 1083 | 4 | 5 | 2013/9/14 10:26 | TARGET SEEMS NOT TO TOUCH MEAT DISH. | MEAT, NO TOUCH |
| 1084 | 9 | 7 | 2013/10/14 10:27 | TARGET DID NOT TOUCH FISH DISH WITH CHOPSTICKS. | FISH, NO TOUCH WITH CHOPSTICKS |
| 1085 | 1 | 10 | 2013/8/14 10:30 | TARGET SAID THAT HE/SHE DID NOT WANT TO EAT ANYTHING AND RETURNED TO ROOM. | NOT WANT TO EAT, ROOM |
| 1091 | 4 | 4 | 2013/9/14 10:37 | TARGET HAD POOR APPETITE AND ATE 30% OF PRINCIPLE DISH AND 20% OF SIDE DISH. | APPETITE, PRINCIPLE DISH, % , SIDE DISH, % |
| 1095 | 4 | 4 | 2013/11/21 8:30 | BLOOD PRESSURE IS SLIGHTLY HIGHER THAN USUAL AND TARGET IS UNSTEADY ON HIS/HER FEET. | BLOOD PRESSURE, FEET |
| 1153 | 7 | 2 | 2014/1/13 17:15 | TARGET IS INCLINING TO LEFT DURING MEAL. | MEAL, INCLINE TO LEFT |

FIG.3

MS. FUJIE ABE

[MONTH] WEEK DAY TIMEFRAME

| | THREE MONTHS BEFORE | TWO MONTHS BEFORE | LAST MONTH | THIS MONTH |
|---|---|---|---|---|
| COGNITION | TWO INCIDENTS (THREE KEYWORDS)<br>[SLEEPING, OPENED EYES] OBSERVER STARTS ASSISTING IN TAKING MEAL SO FAR ...<br>[EYES OPEN] TARGET USES LEFT HAND TO HANDLE FLAT NOODLE PUT IN SMALL BOWL .... | THREE INCIDENTS (THREE KEYWORDS)<br>[SLEEPING] SINCE TARGET CANNOT CONCENTRATE ON MEAL AND STARTS SLEEPING ....<br>[CLOSED EYES] TARGET IS SLEEPING WITH EYES CLOSED.<br>[EYES OPEN] OBSERVER LET TARGET DRINK MISO SOUP BY ONE SIP, AND TARGET OPENED EYES .... | FIVE INCIDENTS (EIGHT KEYWORDS)<br>[WANDERING] TARGET WAS WANDERING BY HERSELF AFTER EVENING CARE ....<br>[CLOSED EYES, EYES CLOSED] TODAY, TARGET MOVED MOUTH WITH EYES CLOSED ....<br>[SLEEPING, EYES OPEN] TARGET IS SLEEPING DURING MEAL IN MANY CASES ....<br>[OH_UNSURE] TARGET WENT TO TOILET BEFORE MEAL ....<br>[SLEEPING] TARGET SEEMS TO GET SLEEPY. | SIX INCIDENTS (SIX KEYWORDS)<br>[UNSURE] TARGET IS UNSURE ABOUT HOW TO EAT FISH ....<br>[WANT TO RETURN] TARGET SAYS THAT SHE WANTS TO RETURN TO LIVING ROOM QUICKLY ....<br>[STAY UP] TARGET IS STAYING UP LATER THAN USUAL TODAY.<br>[UNREST] TARGET IS UNRESTFUL BECAUSE SHE FORGOT THAT SHE ORALLY TOOK MEDICINE.<br>[WANT TO RETURN] TARGET COMPLETED MEAL DOWNSTAIRS AND IS NOW UPSTAIRS ....<br>[UNREST] TARGET IS A PERSON WHO BECOMES UNRESTFUL WHEN SHE FORGETS THAT SHE ORALLY TOOK MEDICINE. |
| TUMBLE/FALL | SIX INCIDENTS (SIX KEYWORDS)<br>[STAND] TARGET STOOD UP BECAUSE SHE WANTED TO GO TO TOILET ...<br>[STAND] TARGET COMPLETED MEAL AND STARTED STANDING UP BY HERSELF ....<br>[FEET] TARGET IS STAGGERING ON HER FEET BECAUSE BLOOD PRESSURE IS SLIGHTLY HIGHER THAN USUAL ....<br>[STAND] OBSERVER GUIDED TARGET TO TOILET AND ALLOW TARGET TO ENTER TOILET BECAUSE TARGET COULD NOT BE PATIENT ANY MORE AND STOOD UP ....<br>[INCLINE TO RIGHT] TARGET IS EATING MEAL WHILE INCLINING TO RIGHT<br>[STAND] SINCE TARGET COULD NOT CONTROL TO EVACUATE OR URINATE ANY MORE AND STOOD UP .... | THREE INCIDENTS (THREE KEYWORDS)<br>[FEET] TARGET SITS DOWN WITHOUT CHECKING THINGS AT HER FEET. NEXT<br>[INCLINE TO RIGHT] TARGET INCLINES TO RIGHT DURING MEAL.<br>[INCLINE TO RIGHT] TARGET IS SLIGHTLY INCLINING TO RIGHT. | ONE INCIDENT (ONE KEYWORD)<br>[STAND] TARGET STANDS UP DURING MEAL. BE CAREFUL .... | ONE INCIDENT (ONE KEYWORD)<br>[INCLINE TO RIGHT] TARGET SLIGHTLY INCLINES TO RIGHT. |
| MISSWALLOWING | TWO INCIDENTS (TWO KEYWORDS)<br>[CHOKED] TARGET CHOKED AFTER MEAL.<br>[VOMIT] TARGET VOMITED RICE PORRIDGE. | TWO INCIDENTS (TWO KEYWORDS)<br>[SPILL] TARGET SPILLED FOOD BY A FAIRLY LARGE AMOUNT BUT ATE ALL ....<br>[CHOKED] TARGET PUT BEAN CURD IN MOUTH BUT LEFT A BIT ... | TWO INCIDENTS (TWO KEYWORDS)<br>[VOMIT] TARGET VOMITED MEAT PUT IN MOUTH.<br>[SPILLING FOOD] TARGET SPILLED FOOD ON APRON. | ONE INCIDENT (TWO KEYWORDS)<br>[COUGHING, CHOKED] TARGET COUGHED ONLY WHEN SHE DRANK SOUP ONCE .... |
| NUTRITION | ONE INCIDENT (ONE KEYWORD)<br>[DO NOT WANT TO EAT] TARGET SAID THAT SHE DID NOT WANT TO EAT ANYTHING TODAY AND ... IN ROOM. | TWO INCIDENTS (TWO KEYWORDS)<br>[NO TOUCH] TARGET SEEMS NOT TO TOUCH MEAT.<br>[APPETITE] TARGET HAS POOR APPETITE TODAY AND ... 30% OF PRIMARY DISH AND 20% OF SIDE DISH. | ONE INCIDENT (ONE KEYWORD)<br>[NO TOUCH WITH CHOPSTICKS] TARGET DID NOT TOUCH FISH WITH CHOPSTICKS. | ONE INCIDENT (ONE KEYWORD)<br>[APPETITE] TARGET HAS POOR APPETITE. |

FIG.4

MS. FUJIE ABE

| MONTH | WEEK | DAY | TIMEFRAME |

| | THREE MONTHS BEFORE | TWO MONTHS BEFORE | LAST MONTH | THIS MONTH |
|---|---|---|---|---|
| COGNITION | TWO INCIDENTS (THREE KEYWORDS) [SLEEPING, OPENED EYES] OBSERVER STARTS ASSISTING IN TAKING MEAL SO FAR... [EYES OPEN] TARGET USES LEFT HAND TO HANDLE FLAT NOODLE PUT IN SMALL BOWL... | THREE INCIDENTS (THREE KEYWORDS) [SLEEPING] SINCE TARGET CANNOT CONCENTRATE ON MEAL AND STARTS SLEEPING... [CLOSED EYES] TARGET IS SLEEPING WITH EYES CLOSED. [EYES OPEN] OBSERVER LET TARGET DRINK MISO SOUP BY ONE SIP, AND TARGET OPENED EYES... | FIVE INCIDENTS (EIGHT KEYWORDS) [WANDERING] TARGET WAS WANDERING BY HERSELF AFTER EVENING CARE... [CLOSED EYES, EYES CLOSED] TODAY, TARGET MOVED MOUTH WITH EYES CLOSED... [SLEEPING, EYES OPEN] TARGET IS SLEEPING DURING MEAL IN MANY CASES... [AH, UNSURE] TARGET WENT TO TOILET BEFORE MEAL... [SLEEPING] TARGET SEEMS TO GET SLEEPY. | SIX INCIDENTS (SIX KEYWORDS) [UNSURE] TARGET IS UNSURE ABOUT HOW TO EAT FISH... [WANT TO RETURN] TARGET SAYS THAT SHE WANTS TO RETURN TO LIVING ROOM QUICKLY... [STAY UP] TARGET IS STAYING UP LATER THAN USUAL TODAY. [UNREST] TARGET IS UNRESTFUL BECAUSE SHE FORGOT THAT SHE ORALLY TOOK MEDICINE. [WANT TO RETURN] TARGET COMPLETED MEAL DOWNSTAIRS AND IS NOW UPSTAIRS. [UNREST] TARGET IS A PERSON WHO BECOMES UNRESTFUL WHEN SHE FORGETS THAT SHE ORALLY TOOK MEDICINE. |
| TUMBLE/FALL | SIX INCIDENTS (SIX KEYWORDS) [STAND] TARGET STOOD UP BECAUSE SHE WANTED TO GO TO TOILET... [STAND UP] TARGET COMPLETED MEAL AND STARTED STANDING UP BY HERSELF... [FEET] TARGET IS STAGGERING ON HER FEET BECAUSE BLOOD PRESSURE IS SLIGHTLY HIGHER THAN USUAL... [STAND] OBSERVER GUIDED TARGET TO TOILET AND ALLOW TARGET TO ENTER TOILET BECAUSE TARGET COULD NOT BE PATIENT ANY MORE AND STOOD UP... [INCLINE TO RIGHT] TARGET IS EATING MEAL WHILE INCLINING TO RIGHT [STAND] SINCE TARGET COULD NOT CONTROL TO EVACUATE OR URINATE ANY MORE AND STOOD UP... | THREE INCIDENTS (THREE KEYWORDS) [FEET] TARGET SITS DOWN WITHOUT CHECKING THINGS AT HER FEET. NEXT... [INCLINE TO RIGHT] TARGET INCLINES TO RIGHT DURING MEAL. [INCLINE TO RIGHT] TARGET IS SLIGHTLY INCLINING TO RIGHT. | ONE INCIDENT (ONE KEYWORD) [STAND] TARGET STANDS UP DURING MEAL. BE CAREFUL... | ONE INCIDENT (ONE KEYWORD) [INCLINE TO RIGHT] TARGET SLIGHTLY INCLINES TO RIGHT. |
| MISSWALLOWING | TWO INCIDENTS (TWO KEYWORDS) [CHOKED] TARGET CHOKED AFTER MEAL. [VOMIT] TARGET VOMITED RICE PORRIDGE. | TWO INCIDENTS (TWO KEYWORDS) [SPILL] TARGET SPILLED FOOD BY A FAIRLY LARGE AMOUNT BUT ATE ALL... [CHOKED] TARGET PUT BEAN CURD IN MOUTH BUT LEFT A BIT... | TWO INCIDENTS (TWO KEYWORDS) [VOMIT] TARGET VOMITED MEAT PUT IN MOUTH. [SPILLING FOOD] TARGET SPILLED FOOD ON APRON. | ONE INCIDENT (TWO KEYWORDS) [COUGHING, CHOKED] TARGET COUGHED ONLY WHEN SHE DRANK SOUP ONCE... |
| NUTRITION | ONE INCIDENT (ONE KEYWORD) [DO NOT WANT TO EAT] TARGET SAID THAT SHE DID NOT WANT TO EAT ANYTHING TODAY AND ... IN ROOM. | TWO INCIDENTS (TWO KEYWORDS) [NO TOUCH] TARGET SEEMS NOT TO TOUCH MEAT. [APPETITE] TARGET HAS POOR APPETITE TODAY AND ... 30% OF PRIMARY DISH AND 20% OF SIDE DISH. | ONE INCIDENT (ONE KEYWORD) [NO TOUCH] TARGET DID NOT TOUCH FISH WITH CHOPSTICKS. | ONE INCIDENT (ONE KEYWORD) [APPETITE] TARGET HAS POOR APPETITE. |

FIG.5

MS. FUJIE ABE    FROM OCTOBER 2013 TO MARCH 2014 (SIX MONTHS)

| MONTH | WEEK | DAY | TIMEFRAME |

| | 8:00 ~ 12:00 | 12:00 ~ 16:00 | 16:00 ~ 20:00 | 20:00 ~ 8:00 |
|---|---|---|---|---|
| COGNITION | TWO INCIDENTS (THREE KEYWORDS) [SLEEPING, OPENED EYES] OBSERVER STARTS ASSISTING IN TAKING MEAL SO FAR ... [EYES OPEN] TARGET USES LEFT HAND TO HANDLE FLAT NOODLE PUT IN SMALL BOWL ... | SIX INCIDENTS (SIX KEYWORDS) [UNSURE] TARGET IS UNSURE ABOUT HOW TO EAT FISH ... [WANT TO RETURN] TARGET SAYS THAT SHE WANTS TO RETURN TO LIVING ROOM QUICKLY ... [STAY UP] TARGET IS STAYING UP LATER THAN USUAL TODAY ... [UNREST] TARGET IS UNRESTFUL BECAUSE SHE FORGOT THAT SHE ORALLY TOOK MEDICINE ... [WANT TO RETURN] TARGET COMPLETED MEAL DOWNSTAIRS AND IS NOW UPSTAIRS ... [UNREST] TARGET IS A PERSON WHO BECOMES UNRESTFUL WHEN SHE FORGETS THAT SHE ORALLY TOOK MEDICINE. | THREE INCIDENTS (THREE KEYWORDS) [SLEEPING] SINCE TARGET CANNOT CONCENTRATE ON MEAL AND STARTS SLEEPING ... [CLOSED EYES] TARGET IS SLEEPING WITH EYES CLOSED. [EYES OPEN] OBSERVER LEFT TARGET DRINK MISO SOUP BY ONE SIP, AND TARGET OPENED EYES ... | FIVE INCIDENTS (EIGHT KEYWORDS) [WANDERING] TARGET WAS WANDERING BY HERSELF AFTER EVENING CARE ... [CLOSED EYES, EYES CLOSED] TODAY, TARGET ... MOUTH WITH EYES CLOSED ... [SLEEPING, EYES OPEN] TARGET IS SLEEPING DURING MEAL IN MANY CASES ... [AH, UNSURE] TARGET WENT TO TOILET BEFORE MEAL ... [SLEEPING] TARGET SEEMS TO GET SLEEPY. |
| TUMBLE/FALL | SIX INCIDENTS (SIX KEYWORDS) [STAND] TARGET STOOD UP BECAUSE SHE WANTED TO GO TO TOILET ... [STAND UP] TARGET COMPLETED MEAL AND STARTED STANDING UP BY HERSELF ... [FEET] TARGET IS STAGGERING ON HER FEET BECAUSE BLOOD PRESSURE IS SLIGHTLY HIGHER THAN USUAL ... [STAND] OBSERVER GUIDED TARGET TO TOILET BECAUSE TARGET COULD NOT BE PATIENT ANY MORE ... [INCLINE TO RIGHT] TARGET IS EATING MEAL WHILE INCLINING TO RIGHT ... [STAND] SINCE TARGET COULD NOT CONTROL TO EVACUATE OR URINATE ANY MORE AND STOOD UP ... | TWO INCIDENT (THREE KEYWORDS) [FEET, STAGGERING] BLOOD PRESSURE IS SLIGHTLY HIGHER THAN USUAL AND TARGET IS STAGGERING ... [INCLINE TO RIGHT] TARGET SLIGHTLY INCLINES TO RIGHT. | THREE INCIDENTS (THREE KEYWORDS) [FEET] TARGET SITS DOWN WITHOUT CHECKING THINGS AT HER FEET ... [INCLINE TO RIGHT] TARGET INCLINES TO RIGHT DURING MEAL ... [INCLINE TO RIGHT] TARGET IS SLIGHTLY INCLINING TO RIGHT. | ONE INCIDENT (ONE KEYWORD) [STAND] TARGET STANDS UP DURING MEAL. BE CAREFUL ... |
| MISSWALLOWING | TWO INCIDENTS (TWO KEYWORDS) [CHOKED] TARGET CHOKED AFTER MEAL ... [VOMIT] TARGET VOMITED RICE PORRIDGE. | ONE INCIDENT (TWO KEYWORDS) [COUGHING, CHOKED] TARGET COUGHED ONLY WHEN SHE DRANK SOUP ONCE ... | TWO INCIDENTS (TWO KEYWORDS) [SPILL] TARGET SPILLED FOOD BY A FAIRLY LARGE AMOUNT BUT ALL ... [CHOKED] TARGET PUT BEAN CURD IN MOUTH BUT ... A BIT ... | TWO INCIDENTS (TWO KEYWORDS) [VOMIT] TARGET VOMITED MEAT PUT IN MOUTH. [SPILLING FOOD] TARGET SPILLED FOOD ON APRON. |
| NUTRITION | ONE INCIDENT (ONE KEYWORD) [DO NOT WANT TO EAT] TARGET SAID THAT SHE DID NOT WANT TO EAT ANYTHING TODAY ... | ONE INCIDENT (ONE KEYWORD) [APPETITE] TARGET HAS POOR APPETITE. PRESCRIBE MEDICINE ... | TWO INCIDENTS (TWO KEYWORDS) [NO TOUCH] TARGET SEEMS NOT TO TOUCH MEAT. [APPETITE] TARGET HAS POOR APPETITE TODAY AND ... 30% OF PRIMARY DISH AND ... SIDE DISH. | ONE INCIDENT (ONE KEYWORD) [NO TOUCH WITH CHOPSTICKS] TARGET DID NOT TOUCH FISH WITH CHOPSTICKS. |

FIG.6

MS. FUJIE ABE  FROM OCTOBER 2013 TO MARCH 2014 (SIX MONTHS)

| | DOCTOR YAMADA | NURSE TANAKA | PHARMACIST SUZUKI | CARE GIVER AIDA |
|---|---|---|---|---|
| COGNITION | TWO INCIDENTS (THREE KEYWORDS) [SLEEPING, OPENED EYES] OBSERVER STARTS ASSISTING IN TAKING MEAL ... [EYES OPEN] TARGET USES LEFT HAND TO ... FLAT NOODLE PUT IN SMALL BOWL ... | SIX INCIDENTS (SIX KEYWORDS) [UNSURE] TARGET IS UNSURE ABOUT HOW TO EAT FISH ... [WANT TO RETURN] TARGET SAYS THAT SHE WANTS TO RETURN TO LIVING ROOM QUICKLY ... [STAY UP] TARGET IS STAYING UP LATER THAN USUAL TODAY ... [UNREST] TARGET IS UNRESTFUL BECAUSE SHE FORGOT THAT SHE ORALLY TOOK MEDICINE. [WANT TO RETURN] TARGET COMPLETED MEAL DOWNSTAIRS AND IS UPSTAIRS ... [UNREST] TARGET IS UNRESTFUL BECAUSE SHE FORGOT THAT SHE ORALLY TOOK MEDICINE ... | THREE INCIDENTS (THREE KEYWORDS) [SLEEPING] SINCE TARGET CANNOT CONCENTRATE ON MEAL AND STARTS SLEEPING ... [CLOSED EYES] TARGET IS SLEEPING WITH EYES CLOSED. [EYES OPEN] OBSERVER LEFT TARGET DRINK MISO SOUP BY ONE SIP, AND TARGET ... EYES. | FIVE INCIDENTS (EIGHT KEYWORDS) [WANDERING] TARGET WAS WANDERING BY HERSELF AFTER EVENING CARE ... [CLOSED EYES, EYES CLOSED] TODAY, TARGET ... MOUTH WITH EYES CLOSED ... [SLEEPING, EYES OPEN] TARGET IS SLEEPING DURING MEAL IN MANY CASES ... [AH, UNSURE] TARGET WENT TO TOILET BEFORE MEAL ... [SLEEPING] TARGET SEEMS TO GET SLEEPY. |
| TUMBLE/FALL | SIX INCIDENTS (SIX KEYWORDS) [STAND] TARGET STOOD UP BECAUSE SHE WANTED TO GO TO TOILET ... [STAND UP] TARGET COMPLETED MEAL AND STARTED STANDING UP BY HERSELF ... [FEET] TARGET IS STAGGERING ON HER FEET BECAUSE BLOOD PRESSURE IS SLIGHTLY HIGHER THAN USUAL. [STAND] ... TOILET BECAUSE TARGET COULD NOT BE PATIENT ANY MORE AND STOOD UP ... [INCLINE TO RIGHT] TARGET IS EATING MEAL WHILE INCLINING TO RIGHT ... [STAND] SINCE TARGET COULD NOT CONTROL TO EVACUATE OR URINATE ANY MORE AND STOOD UP ... | TWO INCIDENTS (THREE KEYWORDS) [FEET, STAGGERING] BLOOD PRESSURE IS SLIGHTLY HIGHER THAN USUAL AND HER FEET ... [INCLINE TO RIGHT] TARGET SLIGHTLY INCLINES TO RIGHT. | THREE INCIDENTS (THREE KEYWORDS) [FEET] TARGET SITS DOWN WITHOUT CHECKING THINGS AT HER FEET ... [INCLINE TO RIGHT] TARGET INCLINES TO RIGHT DURING MEAL ... [INCLINE TO RIGHT] TARGET IS SLIGHTLY INCLINING TO RIGHT. | ONE INCIDENT (ONE KEYWORD) [STAND] TARGET STANDS UP DURING MEAL. |
| MISSWALLOWING | TWO INCIDENTS (TWO KEYWORDS) [CHOKED] TARGET CHOKED AFTER MEAL. [VOMIT] TARGET VOMITED RICE PORRIDGE. | ONE INCIDENT (TWO KEYWORDS) [COUGHING, CHOKED] ... ONLY WHEN SHE DRANK SOUP ONCE ... | TWO INCIDENTS (TWO KEYWORDS) [SPILL] TARGET SPILLED FOOD BY A FAIRLY LARGE AMOUNT BUT ... [CHOKED] TARGET PUT BEAN CURD IN MOUTH BUT ... | TWO INCIDENTS (TWO KEYWORDS) [VOMIT] TARGET VOMITED MEAT PUT IN MOUTH ... [SPILLING FOOD] TARGET SPILLED FOOD ON APRON. |
| NUTRITION | ONE INCIDENT (ONE KEYWORD) [DO NOT WANT TO EAT] TARGET SAID THAT SHE DID NOT WANT TO EAT ANYTHING TODAY ... | ONE INCIDENT (ONE KEYWORD) [APPETITE] TARGET HAS POOR APPETITE. PRESCRIBE MEDICINE ... | TWO INCIDENTS (TWO KEYWORDS) [NO TOUCH] TARGET SEEMS NOT TO TOUCH MEAT. [APPETITE] TARGET HAS POOR APPETITE TODAY AND ... 30% OF PRIMARY DISH ... | ONE INCIDENT (ONE KEYWORD) [NO TOUCH WITH CHOPSTICKS] TARGET DID NOT TOUCH FISH WITH CHOPSTICKS. |

FIG.7

MS. FUJIE ABE FROM OCTOBER 2013 TO MARCH 2014 (SIX MONTHS)

| | DOCTOR | NURSE | PHARMACIST | CARE GIVER |
|---|---|---|---|---|
| COGNITION | TWO INCIDENTS (THREE KEYWORDS) SLEEPING, OPENED EYES] OBSERVER STARTS ASSISTING IN TAKING MEAL … [EYES OPEN] TARGET USES LEFT HAND TO … FLAT NOODLE PUT IN SMALL BOWL … | SIX INCIDENTS (SIX KEYWORDS) [UNSURE] TARGET IS UNSURE ABOUT HOW TO EAT FISH … [WANT TO RETURN] TARGET SAYS THAT SHE WANTS TO RETURN TO LIVING ROOM QUICKLY … [STAY UP] TARGET IS STAYING UP LATER THAN USUAL TODAY … [UNREST] TARGET IS UNRESTFUL BECAUSE SHE FORGOT THAT SHE ORALLY TOOK MEDICINE … [WANT TO RETURN] TARGET COMPLETED MEAL DOWNSTAIRS AND IS WANT TO RETURN UPSTAIRS [UNREST] TARGET IS UNRESTFUL BECAUSE SHE FORGOT THAT SHE ORALLY TOOK MEDICINE … | THREE INCIDENTS (THREE KEYWORDS) [SLEEPING] SINCE TARGET CANNOT CONCENTRATE ON MEAL AND STARTS SLEEPING … [CLOSED EYES] TARGET IS SLEEPING WITH EYES CLOSED. [EYES OPEN] OBSERVER LET TARGET DRINK MISO SOUP BY ONE SIP, AND TARGET … EYES. | FIVE INCIDENTS (EIGHT KEYWORDS) [WANDERING] TARGET WAS WANDERING BY HERSELF AFTER EVENING CARE … [CLOSED EYES, EYES CLOSED] TODAY, TARGET … MOUTH WITH EYES CLOSED. [SLEEPING, EYES OPEN] TARGET IS SLEEPING DURING MEAL IN MANY CASES … [AH, UNSURE] TARGET WENT TO TOILET BEFORE MEAL … [SLEEPING] TARGET SEEKS TO GET SLEEPY. |
| TUMBLE/FALL | SIX INCIDENTS (SIX KEYWORDS) [STAND] TARGET STOOD UP BECAUSE SHE WANTED TO GO TO TOILET … [STAND UP] TARGET COMPLETED MEAL AND STARTED STANDING UP BY HERSELF … [FEET] TARGET IS STAGGERING ON HER FEET BECAUSE BLOOD PRESSURE IS SLIGHTLY HIGHER THAN USUAL. [STAND] … TOILET BECAUSE TARGET COULD NOT BE PATIENT ANY MORE AND STOOD UP … [INCLINE TO RIGHT] TARGET IS EATING MEAL WHILE INCLINING TO RIGHT … [STAND] SINCE TARGET COULD NOT CONTROL TO EVACUATE OR URINATE ANY MORE AND STOOD UP … | TWO INCIDENTS (ONE KEYWORD) [FEET, STAGGERING] BLOOD PRESSURE IS SLIGHTLY HIGHER THAN USUAL AND HER FEET … [INCLINE TO RIGHT] TARGET SLIGHTLY INCLINES TO RIGHT. | THREE INCIDENTS (THREE KEYWORDS) [FEET] TARGET SITS DOWN WITHOUT CHECKING THINGS AT HER FEET … [INCLINE TO RIGHT] TARGET INCLINES TO RIGHT DURING MEAL. [INCLINE TO RIGHT] TARGET IS SLIGHTLY INCLINING TO RIGHT. | ONE INCIDENT (ONE KEYWORD) [STAND] TARGET STANDS UP DURING MEAL. |
| MISSWALLOWING | TWO INCIDENTS (TWO KEYWORDS) [CHOKED] TARGET CHOKED AFTER MEAL. [VOMIT] TARGET VOMITED RICE PORRIDGE. | ONE INCIDENT (TWO KEYWORDS) [COUGHING, CHOKED] … ONLY WHEN SHE DRANK SOUP ONCE | TWO INCIDENTS (TWO KEYWORDS) [SPILL] TARGET SPILLED FOOD BY A FAIRLY LARGE AMOUNT BUT … [CHOKED] TARGET PUT BEAN CURD IN MOUTH BUT … | TWO INCIDENTS (TWO KEYWORDS) [VOMIT] TARGET VOMITED MEAT PUT IN MOUTH … [SPILLING FOOD] TARGET SPILLED FOOD ON APRON. |
| NUTRITION | ONE INCIDENT (ONE KEYWORD) [DID NOT WANT TO EAT] TARGET SAID THAT SHE DID NOT WANT TO EAT ANYTHING TODAY … | ONE INCIDENT (ONE KEYWORD) [APPETITE] TARGET HAS POOR APPETITE. PRESCRIBE MEDICINE … | TWO INCIDENTS (TWO KEYWORDS) [NO TOUCH] TARGET SEEKS NOT TO TOUCH MEAT. [APPETITE] TARGET HAS POOR APPETITE TODAY AND … 30% OF PRIMARY DISH. | ONE INCIDENT (ONE KEYWORD) [NO TOUCH WITH CHOPSTICKS] TARGET DID NOT TOUCH FISH WITH CHOPSTICKS. |

FIG.8

MS. FUJIE ABE

MONTH / WEEK / DAY / TIMEFRAME

| | THREE WEEKS BEFORE | TWO WEEKS BEFORE | LAST WEEK | THIS WEEK |
|---|---|---|---|---|
| DOCTOR YAMADA | TWO INCIDENTS (THREE KEYWORDS) [SLEEPING, OPENED EYES] OBSERVER STARTS ASSISTING IN TAKING MEAL [EYES OPEN] TARGET USES LEFT HAND TO … FLAT NOODLE PUT IN SMALL BOWL … | SIX INCIDENTS (SIX KEYWORDS) [UNSURE] TARGET IS UNSURE ABOUT HOW TO EAT FISH … [WANT TO RETURN] TARGET SAYS THAT SHE WANTS TO RETURN TO LIVING ROOM QUICKLY … [STAY UP] TARGET IS STAYING UP LATER THAN USUAL TODAY … [UNREST] TARGET IS UNRESTFUL BECAUSE SHE FORGOT THAT SHE ORALLY TOOK MEDICINE … [WANT TO RETURN] TARGET COMPLETED MEAL DOWNSTAIRS AND IS UPSTAIRS … [UNREST] TARGET IS UNRESTFUL BECAUSE SHE FORGOT THAT SHE ORALLY TOOK MEDICINE … | THREE INCIDENTS (THREE KEYWORDS) [SLEEPING] SINCE TARGET CANNOT CONCENTRATE ON MEAL AND STARTS SLEEPING … [CLOSED EYES] TARGET IS SLEEPING WITH EYES CLOSED … [EYES OPEN] OBSERVER LET TARGET DRINK MISO SOUP BY ONE SIP, AND TARGET … EYES. | FIVE INCIDENTS (EIGHT KEYWORDS) [WANDERING] TARGET WAS WANDERING BY HERSELF AFTER EVENING CARE … [CLOSED EYES, EYES CLOSED] TODAY, TARGET … MOUTH WITH EYES CLOSED … [SLEEPING, EYES OPEN] TARGET IS SLEEPING DURING MEAL IN MANY CASES … [AH, UNSURE] TARGET WENT TO TOILET BEFORE MEAL … [SLEEPING] TARGET SEEMS TO GET SLEEPY. |
| NURSE TANAKA | SIX INCIDENTS (SIX KEYWORDS) [STAND] TARGET STOOD UP BECAUSE SHE WANTED TO GO TO TOILET … [STAND UP] TARGET COMPLETED MEAL AND STARTED STANDING UP BY HERSELF … [FEET] TARGET IS STAGGERING ON HER FEET BECAUSE BLOOD PRESSURE IS SLIGHTLY HIGHER THAN USUAL … [STAND] … TOILET BECAUSE TARGET COULD NOT BE PATIENT ANY MORE AND STOOD UP … [INCLINE TO RIGHT] TARGET IS EATING MEAL WHILE INCLINING TO RIGHT … [STAND] SINCE TARGET COULD NOT CONTROL TO EVACUATE OR URINATE ANY MORE AND STOOD UP … | TWO INCIDENT (THREE KEYWORD) [FEET, STAGGERING] BLOOD PRESSURE IS SLIGHTLY HIGHER THAN USUAL AND HER FEET … [INCLINE TO RIGHT] TARGET SLIGHTLY INCLINES TO RIGHT. | THREE INCIDENTS (THREE KEYWORDS) [FEET] TARGET SITS DOWN WITHOUT CHECKING THINGS AT HER FEET … [INCLINE TO RIGHT] TARGET INCLINES TO RIGHT DURING MEAL. [INCLINE TO RIGHT] TARGET IS SLIGHTLY INCLINING TO RIGHT. | ONE INCIDENT (ONE KEYWORD) [STAND] TARGET STANDS UP DURING MEAL. |
| PHARMACIST SUZUKI | TWO INCIDENTS (TWO KEYWORDS) [CHOKED] TARGET CHOKED AFTER MEAL. [VOMIT] TARGET VOMITED RICE PORRIDGE. | ONE INCIDENT (TWO KEYWORDS) [COUGHING, CHOKED] … ONLY WHEN SHE DRANK SOUP ONCE … | TWO INCIDENTS (TWO KEYWORDS) [SPILL] TARGET SPILLED FOOD BY A FAIRLY LARGE AMOUNT BUT … [CHOKED] TARGET PUT BEAN CURD IN MOUTH BUT … | TWO INCIDENTS (TWO KEYWORDS) [VOMIT] TARGET VOMITED MEAT PUT IN MOUTH … [SPILLING FOOD] TARGET SPILLED FOOD ON APRON. |
| CARE GIVER AIDA | ONE INCIDENT (ONE KEYWORD) [DO NOT WANT TO EAT] TARGET SAID THAT SHE DID NOT WANT TO EAT ANYTHING TODAY … | ONE INCIDENT (ONE KEYWORD) [APPETITE] TARGET HAS POOR APPETITE. PRESCRIBE MEDICINE … | TWO INCIDENTS (TWO KEYWORDS) [NO TOUCH] TARGET SEEMS NOT TO TOUCH MEAT. [APPETITE] TARGET HAS POOR APPETITE TODAY AND … 30% OF PRIMARY DISH … | ONE INCIDENT (ONE KEYWORD) [NO TOUCH WITH CHOPSTICK] TARGET DID NOT TOUCH FISH WITH CHOPSTICKS. |

FIG.9

| STATE | KEYWORD | RELEVANT LEVEL |
|---|---|---|
| COGNITION | WANDERING | 1.0 |
| COGNITION | UNREST | 0.7 |
| COGNITION | SPILLING FOOD | 0.5 |
| NUTRITION | SPILLING FOOD | 1.0 |
| MISSWALLOWING | SPILLING FOOD | 0.9 |
| MISSWALLOWING | CHOKED | 1.0 |
| TUMBLE/FALL | STUMBLE | 1.0 |
| TUMBLE/FALL | STAGGER | 0.9 |

FIG.13

INFORMATION PROCESSING APPARATUS AND INFORMATION PROCESSING METHOD

FIELD

Embodiments of the present invention relate to an information processing apparatus and an information processing method.

BACKGROUND

In home medical treatment and care, a plurality of staffs of medical treatment and care professions are involved in care and daily lives of patients and care receivers. In the activity of the plurality of staffs, they observe and diagnose the state of each of the patients and care receivers. However, one staff does not continuously or persistently observe a patient but a plurality of staffs of different types of professions visit and observe a patient on different dates at different time intervals. In this case, to allow the plurality of staffs to share information on the patient, results of the observation of the patient are registered in an electronic clinical record, a nursing/care recording system, or an SNS.

As a system for sharing results of the observation of a patient, there is a known information sharing system using voice messages (hereinafter referred to as voice tweet system). In the voice tweet system, each staff tweets a result of the observation of a patient into a microphone of a mobile terminal, such as a smartphone and records the result by using a voice tweet registration application installed in the mobile terminal to create a voice message. The created voice message is transmitted to a server. In the server, a target patient ID of the patient having been tweeted about, a staff ID of the tweeter (speaker), the time when the tweet occurred, the location where the tweet occurred, a keyword extracted from the voice message, and other factors are added as tags to the voice message. Information formed of the voice message, the tags, and other factors is called a voice tweet. Each staff can browse or listen to voice tweets accumulated in the server via a mobile terminal or a personal computer.

There is a demand for desire to grasp the state of a patient, such as changes in a cognitive state and ADL (activity of daily living) of a patient, from results of the observation accumulated in the information sharing system. To grasp the state of a patient, however, it is necessary to search an enormous amount of accumulated data, and it is therefore difficult to grasp the state of a patient in an efficient manner.

Patent Literature 1: Japanese Patent Laid-Open No. 2012-226449

Patent Literature 2: Japanese Patent No. 5,414,865

The embodiments of the present invention are to allow the state of an observed target, such as a patient and a care receiver, to be readily grasped.

SUMMARY

According to one embodiment, an information processing apparatus includes: a first storage to store correspondence data that includes a plurality of mental and physical states and keywords related to each of the states; a second storage to store messages representing contents tweeted for an observed target by a plurality of observers; and a data processor to detect keywords related to each of the states from the messages based on the correspondence data and create presentation information which includes information data arranged correspondingly to each of the states wherein the information data is arranged for each of the messages including the keywords related to the corresponding state and includes the keyword detected from the each of the messages.

BRIEF DESCRIPTION OF THE DRAWINGS

FIG. 2 shows a state-keyword correspondence table according to the embodiment of the present invention;

FIG. 3 shows a voice tweet data table according to the embodiment of the present invention;

FIG. 4 shows presentation information according to the embodiment of the present invention;

FIG. 5 shows an example in which the color of a cell is changed in the presentation information in FIG. 4;

FIG. 6 shows another example of the presentation information according to the embodiment of the present invention;

FIG. 7 shows still another example of the presentation information according to the embodiment of the present invention;

FIG. 8 shows still another example of the presentation information according to the embodiment of the present invention;

FIG. 9 shows still another example of the presentation information according to the embodiment of the present invention;

FIG. 13 shows another example of the state-keyword correspondence table according to the embodiment of the present invention.

DETAILED DESCRIPTION

Below, embodiments will be described with reference to the drawings.

First Embodiment

Figure 1:
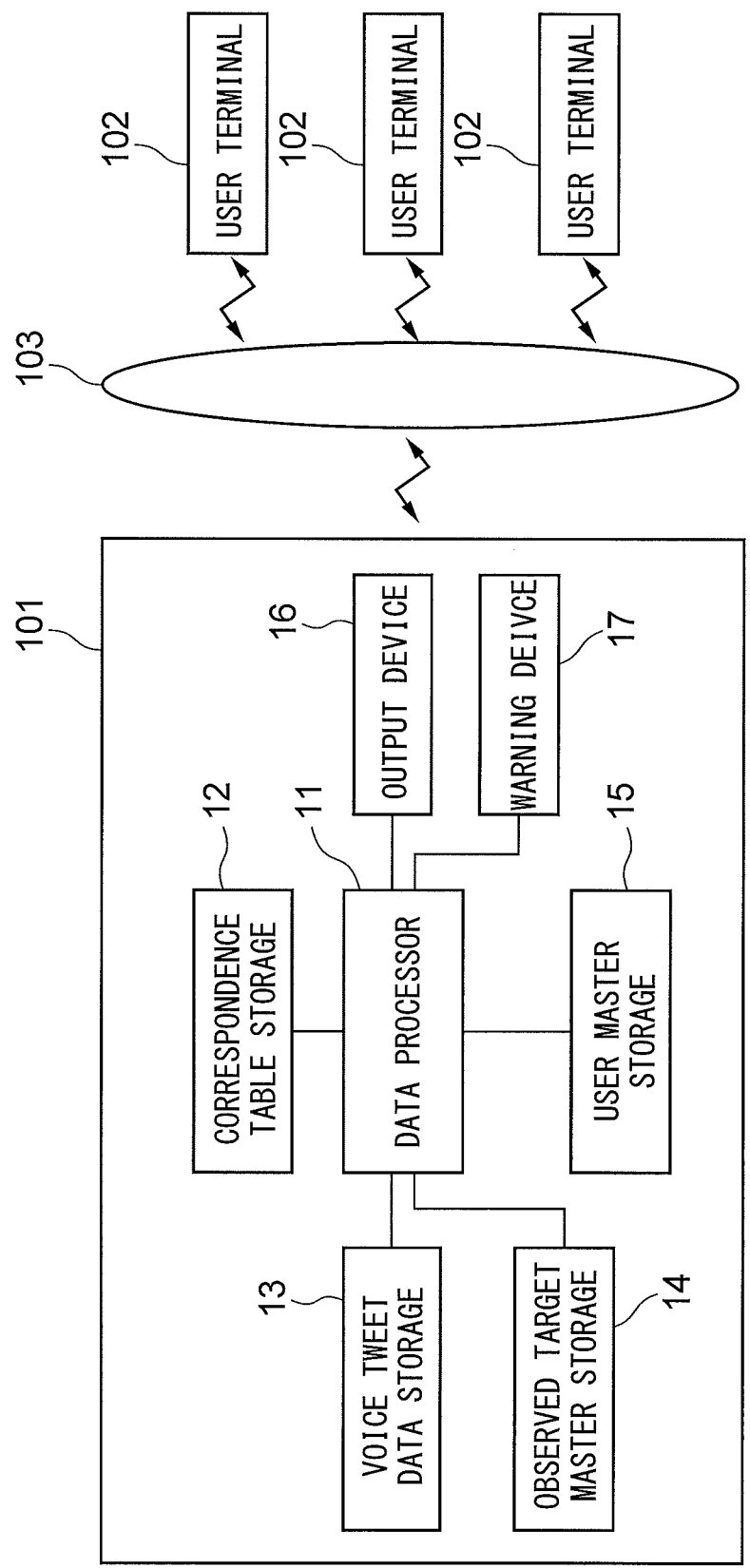
FIG. 1 shows an information processing system including an information processing apparatus according to an embodiment of the present invention.

FIG. 1 shows an information processing system according to an embodiment of the present invention.

The information processing system shown in FIG. 1 includes an information processing apparatus 101 and a plurality of user terminals 102. The information processing apparatus 101 is connected to the plurality of user terminals 102 via a network 103.

The network 103 may have any of the following forms: a wired network; a wireless network; and a wired/wireless hybrid network. Further, the network 103 may be a local network or a wide area network, such as the Internet.

Each of the user terminals is a terminal operated by the user in the present embodiment and is, for example, a smartphone, a PDA, a mobile terminal, or a personal PC. Each of the user terminals includes a CPU, a storage, a display that displays an image, a loudspeaker, a microphone, and other components. The user in the present embodiment is an observer who observes an observed target, such as a patient and a care receiver. Specifically, the observer is, for example, a doctor, a nurse, a care giver, and a pharmacist who are involved in a medical profession, a care profession, and other professions.

The information processing apparatus 101 includes a data processor 11, a correspondence table storage 12, a voice tweet data storage 13, an observed target master storage 14, a user master storage 15, an output device 16, and a warning device 17.

The correspondence table storage 12 stores a state-keyword correspondence table that includes a plurality of mental and physical states of an observed target and a plurality of keywords related to the states where examples of the mental and physical states are acts, utterance, and appearances or the state of a diseased site. The correspondence table storage 12 is connected to the data processor 11. FIG. 2 shows an example of the state-keyword correspondence table.

The states are mental and physical states, and "cognition", "nutrition", "misswallowing", "fall", and other states are presented in the description. The keyword is a word expressed by the observer as a result of the observation of the mind and body of the observed target, such as acts, tweets, and appearances or a state of a diseased site considered to be highly related to the mental and physical state. For example, a keyword "wandering" is highly related to the state "cognition". Each keyword can belong to two or more states. For example, a keyword "spilling food" belongs to three states, "cognition", "misswallowing", and "nutrition". Further, each state may have a hierarchic structure formed of two or more hierarchies. For example, "cognition" may be set as an upper state, and "meal", "daily living", "bathing", and other lower states may be present below "cognition".

The observed target master storage 14 stores an observed target master that includes the IDs of a plurality of observed targets (such as patients and care receivers), the names of the observed targets, and other factors of the observed targets. The observed target master storage 14 is connected to the data processor 11. The observed target master may contain the age, the gender, and other factors in addition to the information described above.

The user master storage 15 stores a user master relating to users of services provided by the information processing apparatus. The user master storage 15 is connected to the data processor 11. The user are doctors, nurses, care givers, pharmacists, and other observers who observe an observed target (such as patient and care receiver), as described above. The user master memorizes the ID, the name, the profession, and other factors of each of the observers. The user master may further memorize, as required, for example, a password necessary for authentication at the time of login to the services provided by the information processing apparatus. In this case, the present apparatus may provide only a user who has inputted a correct observer ID and password with the services.

The voice tweet data storage 13 includes a voice tweet data table. The voice tweet data storage 13 is connected to the data processor 11. The voice tweet data table registers data on voice tweets tweeted (or spoken) by a plurality of observers. FIG. 3 shows an example of the voice tweet data table.

The voice tweet data is formed of the following fields: "voice tweet ID"; "observer ID"; "observed target ID"; "tweet date and time", "content of voice tweet", and "related keyword".

The "voice tweet ID" is an identifier for identifying voice tweet data.

The "observer ID" is an identifier (user ID) for identifying an observer, such as a doctor and a care giver.

The "observed target ID" is an identifier for identifying an observed target, such as a patient and a care receiver.

The "tweet date and time" is the date and time when the observer tweeted the content shown in the "content of voice tweet" field.

The "content of voice tweet" is a message in the form of a text of data on a voice message spoken (tweeted) by the observer or a text of the voice message. The "content of voice tweet" field may memorize both a voice message and a text message. The "content of voice tweet" field may instead memorize a link (such as URL) to a voice message along with a text message. In this case, the voice message may be so memorized in a link-destination server as to be downloadable by a user terminal 102 from the server. It is assumed here that the "content of voice tweet" field memorizes at least a text message.

The "related keyword" is a keyword extracted by the data processor 11, which will be described later, from a voice message or a text message in a keyword extraction process. It is assumed that an extracted keyword coincides with the value in the "keyword" field in the state-keyword correspondence table. It is, however, noted that the assumption is only an example, and a keyword may be extracted by using another reference. In the present example, when a plurality of keywords are extracted, the keywords are so arranged as to be separated with comma, and the separated keywords are memorized in a single "related keyword" field. An extracted keyword can instead be memorized in another form. For example, a table formed of the voice tweet ID field and an "related keyword" field that memorizes only one keyword may be provided, and a single keyword may be memorized in each "related keyword" field one by one.

The data processor 11 communicates with each of the user terminals 102 and carries out a voice tweet data registration process. Each observer observes a patient or a care receiver, specifies an observed target ID, and tweets results of the observation into the microphone of the user terminal 102. The results of the observation include results of the observation of observation items, things that the observer noticed (noticed items) in the observation of the observation items, and other factors. The content of a tweet is registered in the form of a voice message by an application installed in the terminal. The application adds the voice tweet ID, the observer ID, the observed target ID, the tweet date and time, and other tags to the voice message and transmits the resultant voice message to the present information processing apparatus. The data processor 11 of the present apparatus converts the voice message into a text in a voice recognition process to produce a text message. The data processor 11 further extracts a keyword from the voice message or the text message. In the keyword extraction, differences in wording (conjugation) of a word/term are absorbed for the keyword extraction. For example, "stagger", "staggering", "having staggered", and other conjunctions are all extracted as the "stagger". This is achieved by morphological analysis in which the stem of a word is extracted. Further, a hash table can be used to perform conversion into a different expression, such as conversion of "stagger" into "unstableness" (in this example, the key and value of the hash table are registered as "stagger" and "unstableness", respectively). The data processor 11 registers the voice tweet ID, the observer ID, the observed target ID, the tweet date and time, the content of the voice tweet (voice message and/or text message), and the extracted keyword as voice tweet data in the voice tweet data table. The conversion of a voice message into a text may be performed by a user terminal, and the converted text message may be transmitted from the user terminal to the present apparatus. The registration of voice tweet data may be performed by an apparatus different from the present information processing apparatus, and the voice tweet data table may be received from the other apparatus.

The data processor 11 receives an observed target ID by specified by a user from a user terminal 102 and processes voice tweet data having the specified observed target ID. The data processor 11 can access the correspondence table storage 12, the voice tweet data storage 13, the observed target master storage 14, and the user master storage 15 and can therefore read data memorized in the storages.

The data processor 11 refers to each voice tweet data having the specified observed target ID and identifies, for each state in the state-keyword correspondence table, a keyword related to the state from the "related keyword" field. For example, keywords related to "cognition" include "wondering", "unrest", and "spilling food". Each voice tweet data is checked for identification of the keywords "wondering", "unrest", and "spilling food".

The data processor 11 creates, for each voice tweet data in which a keyword is identified, information data containing the identified keyword and arranges the created information data in association with the corresponding state to create presentation information to be presented to the user. The format of the information data contains a list of identified keywords and a voice tweet body (text message) by way of example. In the following description, the information data has the format described above unless otherwise specified.

The output device 16 transmits the presentation information created by the data processor 11 to the user terminal 102 having requested the data processing. The output device 16 is connected to the data processor 11. The user terminal 102 displays an image representing the presentation information on an application screen. The data processor 11 may contain information that identifies a presentation information display method in the presentation information transmitted to the user terminal 102. For example, presentation information may further include information that specifies the color and font size of a keyword contained in each information data, the color of the background in front of which each information data is arranged, the color of a voice tweet body, and other factors.

Instead, the output device 16 may transmit a link (such as URL) to the presentation information to the user terminal 102, and the user terminal 102 may download the presentation information from the link destination and display the presentation information on the screen. In this case, it is assumed that the data processor 11 transmits the created presentation information to a link-destination server.

Still instead, the output device 16 may transmit presentation information in the form of an electronic mail message to the user terminal 102. The output device 16 may still instead output presentation information to a printer for printing or may use any output method other than the methods described above.

Some specific configuration examples of the presentation information will be shown below.

The data processor 11 may further categorize the information data (keyword list, voice tweet body) arranged in association with each state, on the basis of tweet date and time and in accordance with a predetermined time unit and arrange the categorized information data to form presentation information. For example, information data may be categorized on a day basis, a week basis, a month basis, a timeframe basis, or a one-hour basis or by using any of other period units (such as spring, summer, autumn, winter, or any other season unit or every three months) or any of other variety of time units. The time unit may be specified via a user terminal. Further, for each state-based and time-unit-based category, the data processor 11 may sum up the number of pieces of categorized information data, that is, the number of related voice tweets. Moreover, for each of the categories, the total number of listed keywords in a set of the information data may be summed up.

FIG. 4 shows an example in which presentation information created by category of information data on a month basis is displayed on the screen of a user terminal. The vertical axis represents states, and the horizontal axis represents month-based items. The state includes "cognition", "tumble/fall", "misswallowing", and "nutrition". The month item includes "three months before", "two months before", "last month", and "this month". That is, data on voice tweets tweeted in the period over the past three months are shown.

A cell is arranged for each combination of a state and a month item. In each cell, one or more information data are so arranged as to be piled up in such a way that one incident is written in one line. In this example, the information data is expressed in the following format: [<related keyword>, <related keyword>, . . . ]+<voice tweet body>. That is, information data is formed of a list of keywords separated by commas and a voice tweet body. This configuration allows the user to quickly and readily know how many voice tweets related to each state have occurred each month. Further, each cell displays the number of pieces of information data (the number of voice tweets) and the number of keywords in the cell. The format of information data is, however, not limited to the format described above, and information data may be formed, for example, only of a voice tweet body. In this case, in the voice tweet body, a keyword related to a categorized state may be colored differently from the other portions for visual enhancement.

The name of an observed target is displayed in an upper left portion of the screen. Further, "month", "week", "day", and "timeframe" buttons are provided. FIG. 4 shows an example of a case where the "month" button has been selected. When the "week", "day", or "timeframe" button is selected, information data may be categorized at a time unit according to the selected button and the categorized information data may then be displayed.

One voice tweet may contain a plurality of keywords for a plurality of states in some cases. Information data containing the same certain voice tweet may therefore appear in a plurality of cells.

In information data, listed keywords contained in the information data may be displayed in a color different from the color in which the following voice tweet text is displayed. For example, the keywords may be formed of red letters, and the voice tweet text may be formed of black letters.

When one line is not long enough to display a voice tweet text, the voice tweet text is displayed halfway. A screen that displays the entire text may be displayed in the form of a popup by pointing the voice tweet text with a mouse pointer. Instead, when one line is not long enough to display a voice tweet text, the voice tweet text can be displayed in a plurality of lines by starting new lines.

Further, a voice tweet text may be so set as to have a link, and the link may be clicked to reproduce a voice message via a loudspeaker that is not shown.

The observer who looks at the screen shown in FIG. 4 can use information presented on the screen to grasp a change in the state of the observed target. The observer can readily grasp whether the number of voice tweets related to each state tends to increase or decrease. In the case of "cognition", FIG. 4 shows that the number of pieces of information data (the number of voice tweets) increases over a period from the point of time three months ago to this month. FIG. 4 further shows that the number of keywords related to "cognition" spoken by the observer increases. Moreover, the content of a keyword that appears changes as the month advances. Use of such information allows a doctor, a care giver, and other staffs can grasp the cognitive-impairment state of the observed target.

The display color (background color) of a cell can be changed on a cell basis in accordance with the number of summed-up pieces of information data (a total number of voice tweets) in the cell, as shown in FIG. 5. For example, a plurality of ranges are set by using reference values, and the display color of a cell can be changed in accordance with which range the number of voice tweets in the cell belongs to as follows: When the number is greater than or equal to 0 but smaller than or equal to 2, the cell is displayed in white; when the number is greater than or equal to 3 but smaller than or equal to 4, the cell is displayed in light blue; and when the number is greater than or equal to 5, the cell is displayed in indigo. In FIG. 5, the change in the color is expressed by differences in the intervals of the hatched portions. The reference values of the number of voice tweets for changing the display color can be set on a state basis. As a result, the observer can more intuitively grasp a tendency of the change on a state basis, as compared with the display in which information data is merely piled up in a cell. The above description has been made of the case where display color of a cell is changed in accordance with the number of pieces of information data (number of voice tweets) in the cell. Similarly, the display color of a cell can be changed in accordance with the number of keywords in the cell.

In FIGS. 4 and 5, the horizontal axis is drawn on a month basis. Instead, the horizontal axis may be drawn on a week basis or a timeframe basis. FIG. 6 shows an example in which presentation information created by drawing the horizontal axis on a timeframe basis is displayed on the screen of a user terminal. In FIG. 6, the horizontal axis is divided into a morning timeframe (from 8:00 to 12:00), a midday timeframe (from 12:00 to 16:00), an evening timeframe (from 16:00 to 20:00), and the remaining timeframe (from 20:00 to 8:00). Instead, the timeframes may be determined by using another reference.

The above description has been made of the case where information data is categorized by using a time unit on a state basis. Instead, information data may be categorized on a meteorological phenomenon basis. In this case, the vertical axis represents states, and the horizontal axis represents meteorological phenomenon items. To this end, meteorological phenomenon information, such as the temperature, humidity, and weather at the time of tweet, is set in voice tweet data. When voice tweet data is acquired, a tweeted position may be acquired in addition to tweet date and time from a user terminal, and meteorological phenomenon data may be acquired from a meteorological phenomenon server made public to the outside world on the basis of the acquired tweet date and time and tweeted position. The position where the tweet occurred may be added to the voice tweet data.

As another category example, information data can be categorized by using a position related to a tweet. The position can be the tweet position added to the voice tweet described above (for example, the name of a town identified by a reverse geo-coding technology on the basis of GPS latitude and longitude acquired with a smartphone at the time of the tweet) or the name of a town in the address of a target patient. In this case, the vertical axis represents states, and the horizontal axis represents positions. Still instead, the number of tweet incidents on a state basis may be used to create a bar graph, and a bar is arranged in the position on a map (such as a position close to the center of a map of the town).

As still another category example, information data can be categorized on an observer (user) basis. FIG. 7 shows an example in which presentation information in this case is displayed on the screen of a user terminal. The vertical axis represents states, and the horizontal axis represents users. In this example, it is assumed that voice tweet data to be processed are those having created within the period over the past 6 months. Instead, other periods, such as the past 10 days and the past 24 hours, may be used to set voice tweet data to be processed.

As still another category example, information data can be categorized on an observer's (user's) profession basis. FIG. 8 shows an example in which presentation information in this case is displayed on the screen of a user terminal. The vertical axis represents states, and the horizontal axis represents professions. The profession may be identified from the "observer ID" in voice tweet data on the basis of the user master described above.

In each of the category examples described above, the vertical axis always represents states. Instead, the vertical axis may represent the observer (user) or the profession of the observer, and the horizontal axis may represent the time unit. FIG. 9 shows an example in which presentation information created by drawing the vertical axis on an observer basis and the horizontal axis on a week basis is displayed on the screen of a user terminal. In this example, the horizontal axis is drawn on a week basis. Instead, the horizontal axis may be drawn on a month basis or on a timeframe basis or by using any other time unit.

The categorizing methods described above can be combined with each other. For example, information data may be categorized (or classified) on a state basis by using a desired time unit and profession unit. Other combinations may be used.

The warning device 17 in FIG. 1 transmits a warning message to a user terminal 102 in accordance with results of the processes carried out by the data processor 11. The warning device 17 is connected to the data processor 11. As an example, in a case where there is a cell (category) in which the summed-up number of information data or keywords is greater than or equal to a threshold, a warning message is transmitted. The warning message may contain information that identifies the cell (category).

A user terminal 102 having received the warning message displays the received warning message on the screen to prompt the observer to be careful. To display the warning message, the warning message may be displayed in the form of a popup message. In addition to the above, the warning message can be transmitted in the form of an electronic mail message to a user terminal 102. Warning sound output instruction data may be transmitted to a user terminal 102, and the user terminal 102 may reproduce warning sound through a loudspeaker that is not shown.

In the present embodiment, a keyword contained in a voice message or a text message is extracted and memorized in the "related keyword" field. Instead, whenever the presentation information creation process in the present embodiment is carried out, the keyword extraction from a voice message or a text message may be performed. In this case, no keyword is required to be memorized in advance in the "related keyword" field. The computation load increases by the amount corresponding to the keyword extraction when the presentation information creation process is carried out, but the storage region of the voice tweet data storage 13 can be reduced.

Second Embodiment

In the first embodiment, the case where the number of pieces of information data (number of voice tweets) is summed up on a category (cell) basis has been presented. Instead, relative evaluation of whether the number of occurrences of voice tweets about a certain observed target is greater or smaller than the number of occurrences of voice tweets about other observed targets can be performed, and the display color of a cell can be changed in accordance with a result of the evaluation. Specifically, the display color of each cell related to an observed target is determined on the basis of comparison between the number of voice tweets in the cell related to the observed target and the distribution of the number of occurrences of voice tweets categorized on the same conditions for each cell related to all observed targets.

For a state "j" of an observed target "u", the number of occurrences "Nuj" of voice tweets per specified period (per month, for example) is obtained. A distribution of the number of occurrences of voice tweets per specified period is obtained by acquisition of "Nuj" for all observed targets. As the distribution, a histogram may be obtained, or the average and standard deviation may be determined by assuming that the distribution follows a normal distribution. The thus obtained distribution may be saved as data in a file.

The number of occurrences of voice tweets per specified period can be calculated as follows: For each of the observed targets, voice tweets related to each state over a fixed period ("T" denotes the number of days in the fixed period) are summed up, and the summed-up value is divided by the number of days "T" in the period; and the number of occurrences of voice tweets per day on a state basis can be determined for each of the observed targets. The number of occurrences of voice tweets is then multiplied by 14 to produce the number of occurrences of voice tweets per two weeks, and the number is multiplied by 30 to produce the number of occurrences of voice tweets per month. In general, the number of occurrences of related voice tweets per arbitrary period can be calculated.

Figure 11:
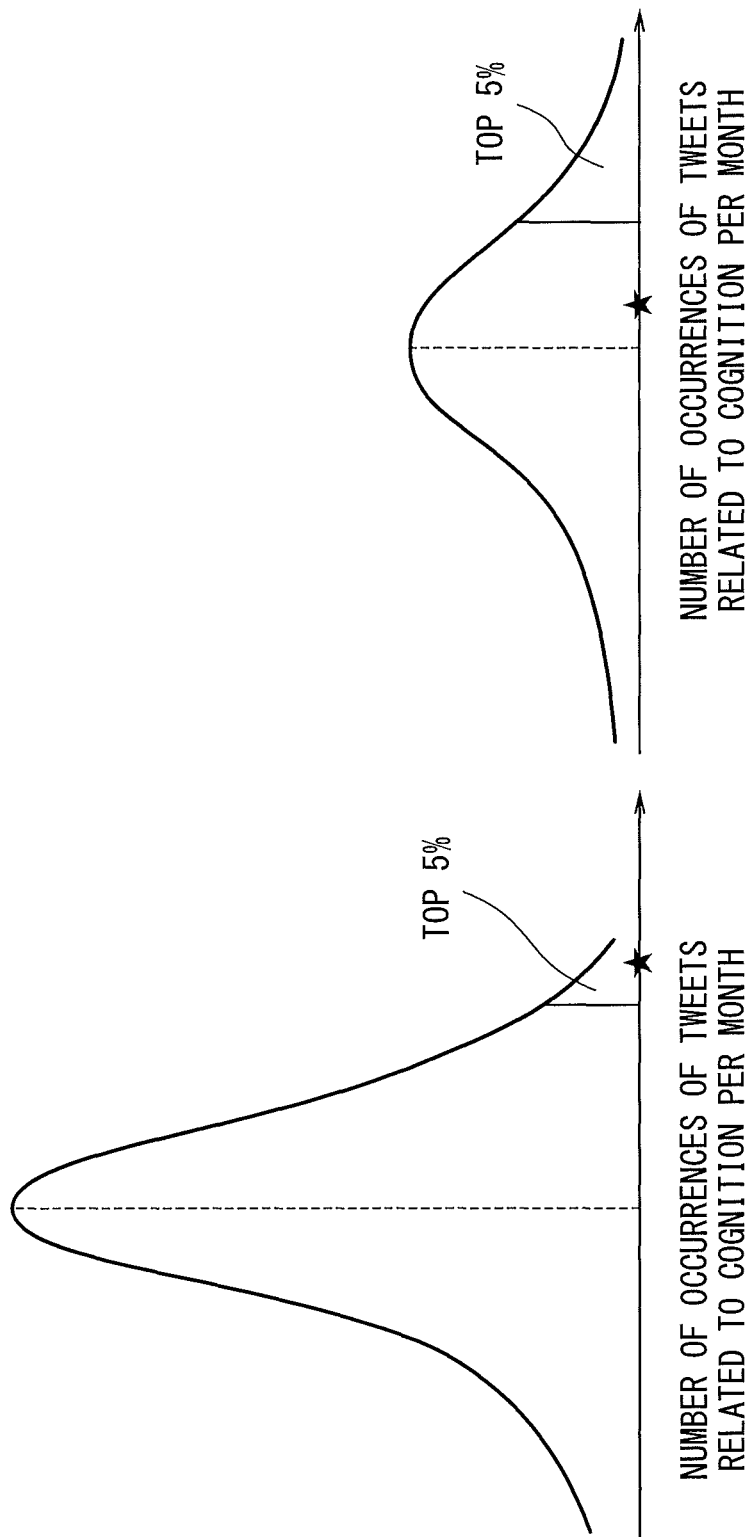
FIGS. 11A and 11B show examples of the distribution of occurrence of keywords related to a plurality of observed targets.

FIG. 11A shows the distribution of the number of occurrences of voice tweets related to "cognition" per month. The horizontal axis represents the number of occurrences of voice tweets related to "cognition", and the vertical axis represents the number of observed targets. The star symbol represents the number of occurrences of voice tweets related to "cognition" of a certain observed target.

Figure 10:
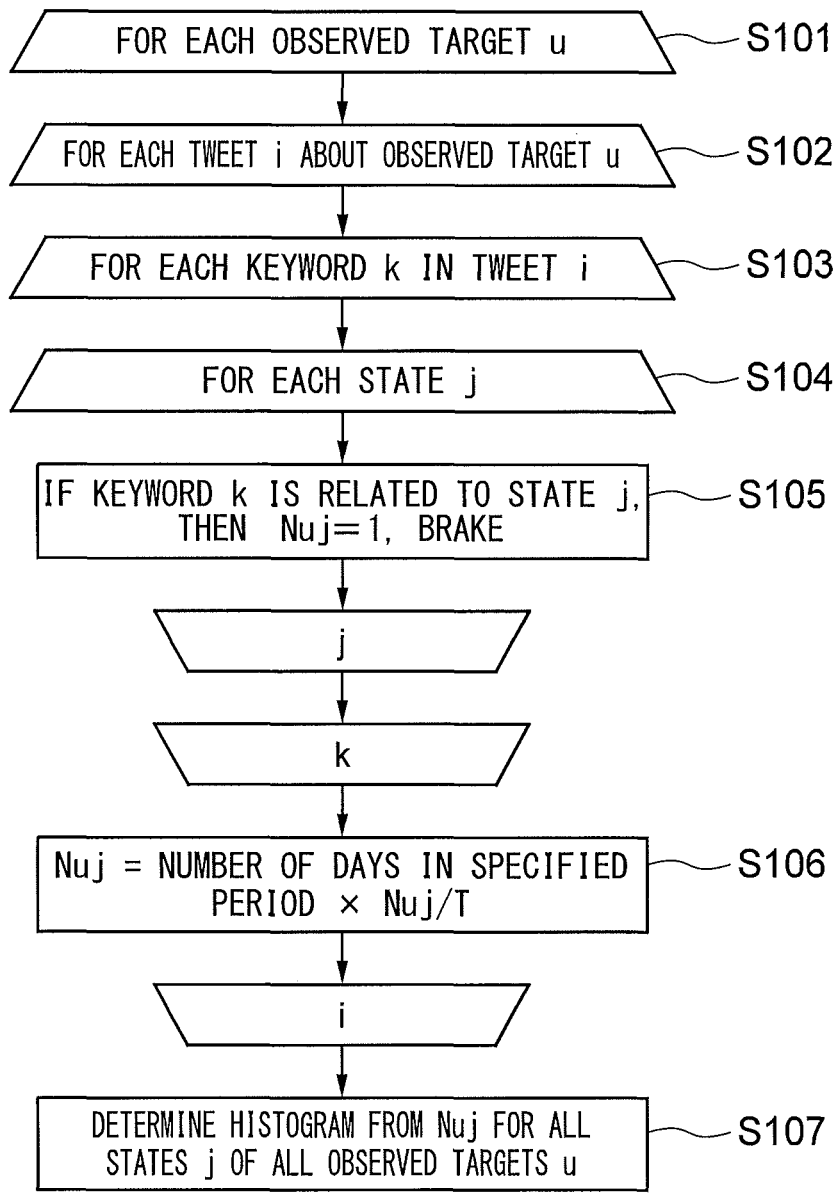
FIG. 10 is a flowchart of the process of calculating the distribution of occurrence of keywords related to a plurality of observed targets.

FIG. 10 is a flowchart of the process of determining the distribution of the number of occurrences of voice tweets about all observed targets per specified period. The present process is carried out by the data processor.

Each voice tweet "i" about an observed target "u" is considered (S101, S102). It is evaluated on the basis of the state-keyword correspondence table in the correspondence table storage 12 whether each keyword "k" in the voice tweet "i" (S103) is related to each state "j" (S104). When a result of the evaluation shows that the keyword "k" is related to the state "j", 1 is added to "Nuj", whereas when a result of the evaluation shows that the keyword "k" is not related to the state "j", no operation is performed (S105). It is, however, noted that in a case where a plurality of keywords "k" are present for the same state "j", 1 is added to "Nuj" only once. The initial value of "Nuj" is set at zero. After the steps described above are carried out for each keyword "k" and each state "j", "Nuj" is divided by the number of days "T" in the fixed period and multiplied by the number of days in the specified period, and the resultant value is used to update "Nuj" (S106). The updated "Nuj" is the number of occurrences of voice tweets about the observed target "u" per the specified period. The process described above is carried out for all observed targets, and the resultant "Nuj" for all observed targets provides the distribution, such as a histogram (S107).

Now, define "Mxyz", which represents the number of occurrences of voice tweets related to a certain state "y" of a certain observed target "x" in a certain month "z". "Mxyz" can be evaluated based on the position thereof in the distribution of "Nuj". For example, in the case where the distribution is obtained in the form of a histogram, where "Mxyz" is located in the "Nuj" distribution, that is, how much top percentage (upper percentile value) corresponds to the point where "Mxyz" is located in the "Nuj" distribution can be determined. The determined value can be used to change the display color of the cell described above.

For example, when "Mxyz" is located in a position in the "Nuj" distribution where the percentile value is greater than or equal to the upper 5 percentile value, as shown in FIG. 11A, the color of the relevant cell can, for example, be set at a specific color (such as red). It can be said that the position where the percentile value is greater than or equal to the upper 5 percentile value is a position where the number of occurrences of voice tweets is fairly greater than the average. The display color may be continuously or discretely changed for each upper percentile value. In a case where the "Nuj" distribution follows a normal distribution, the display color may be changed in accordance with an evaluation value calculated by ("Mxyz"—average "Nuj")/ standard deviation.

Figure 12:
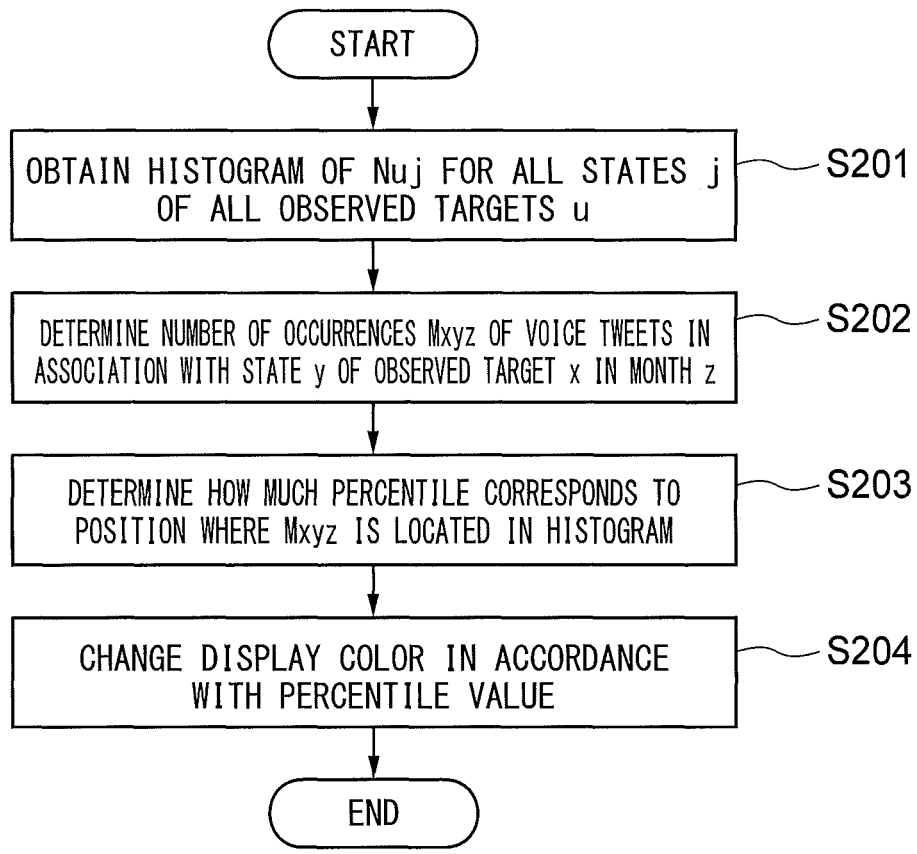
FIG. 12 is a flowchart of the process of changing a display color in accordance with a result of relative evaluation of a certain observed target with respect to a plurality of observed targets.

FIG. 12 is a flowchart of the process of evaluating the number of occurrences of voice tweets about a certain observed target on the basis of the distribution of the number of occurrences of voice tweets about all observed targets. The present process is carried out by the data processor.

A histogram of "Nuj" is obtained for all states "j" of all observed targets "u" (S201). The histogram may be obtained by the process in the flowchart shown in FIG. 10. The number of occurrences of voice tweets related to a state "y" of a certain observed target "x" in a month "z" is determined (S202). How much percentile corresponds to the position where "Mxyz" is located in the histogram is determined (S203). The display color of a cell is changed in accordance with the percentile value (S204).

In the example described above, the number of occurrences of voice tweets about a certain observed target ("x") is evaluated on the basis of the distribution of the number of occurrences of voice tweets about all observed targets. As another example, the distribution of occurrences of voice tweets about observed targets who satisfy a predetermined condition may be used instead of the distribution of the number of occurrences of voice tweets about all observed targets.

Specific examples of the predetermined condition are, for example, as follows:

(1) Observed targets whose age or age group (age width of 10, for example) are equal to those of the observed target "x"

(2) Observed targets whose gender is the same as that of the observed target "x"

(3) Observed targets whose nursing care level is equal to that of the observed target "x" (FIG. 11B shows an example of the distribution in this case. The population parameter in FIG. 11B is smaller than that in FIG. 11A.)

(4) Observed targets who have the same underlying disease that the observed target "x" has (5) Observed targets who receive the same prescribed medicine as that for the observed target "x" in the past "L" months ("L" is integer greater than or equal to 1)

(6) Observed targets who satisfy a combination of part of the conditions described above The age, gender, nursing care level, underlying disease, and other pieces of information may be acquired by connection of the present information processing system to another medical treatment/care system, such as care records and nursing records over a network. Instead, a database that memorizes these pieces of information described above may be incorporated in the information processing apparatus 101 in FIG. 1.

In the example described above, the number of occurrences of voice tweets about a certain observed target is compared with the distribution of the number of occurrences of voice tweets about all observed targets and may instead be compared with the distribution of occurrences of voice tweets about himself/herself (about observed target "x") in the past, for example, the distribution of occurrences of voice tweets about the observed target "x" in the past (five to one year ago, for example).

In the above description, the evaluation is performed on the basis of the number of occurrences of voice tweets. Instead, the evaluation may be performed on the basis of the number of occurrences of keywords (a total number of keywords). The number of occurrences of keywords can be calculated by addition of 1 to "Nuj" for each keyword "k" in a case where a plurality of keywords "k" are present for the same state "j" in the process in step S105 in FIG. 10.

Third Embodiment

FIG. 13 shows a state-keyword correspondence table according to the present embodiment. A "relevant level" field is added to the state-keyword correspondence table according to the first embodiment.

The relevant level is a numeral representing the magnitude of relevance between a state and a keyword. For a certain state, a plurality of keywords related to the state may be present, but it is considered that the depth of the relevance with the state varies depending on a keyword. For example, the keyword "wandering" and the keyword "unrest" are both related to the state of cognition, but "wandering" is considered to be more deeply related to cognition. Therefore, for example, consider a case where five voice tweets containing the keyword "wandering" occur in a certain month and a case where five voice tweets containing the keyword "unrest" occur in the month, and the evaluation is desirably so made that the former tends to be more related to cognition.

To this end, the state-keyword correspondence table is provided with the "relevant level" field in addition to the "state" and "keyword" fields. In the present embodiment, the relevant level is used to extend the method for summing up the number of voice tweets or the number of keywords shown in the first embodiment.

In the present embodiment, the relevant level has a value greater than 0 but smaller than or equal to 1. The relevant level is, however, not necessarily defined as described above. The relevant level may be defined for all keywords on a state basis. In this case, a keyword that is not at all related to the state may be defined to have a relevant level of 0. In a case where the depth of relevance is not considered but only existence or non-existence of relevance is considered, the relevant level may not be used as in the first embodiment, and only keywords related to each state may be associated with the state.

Figure 14:
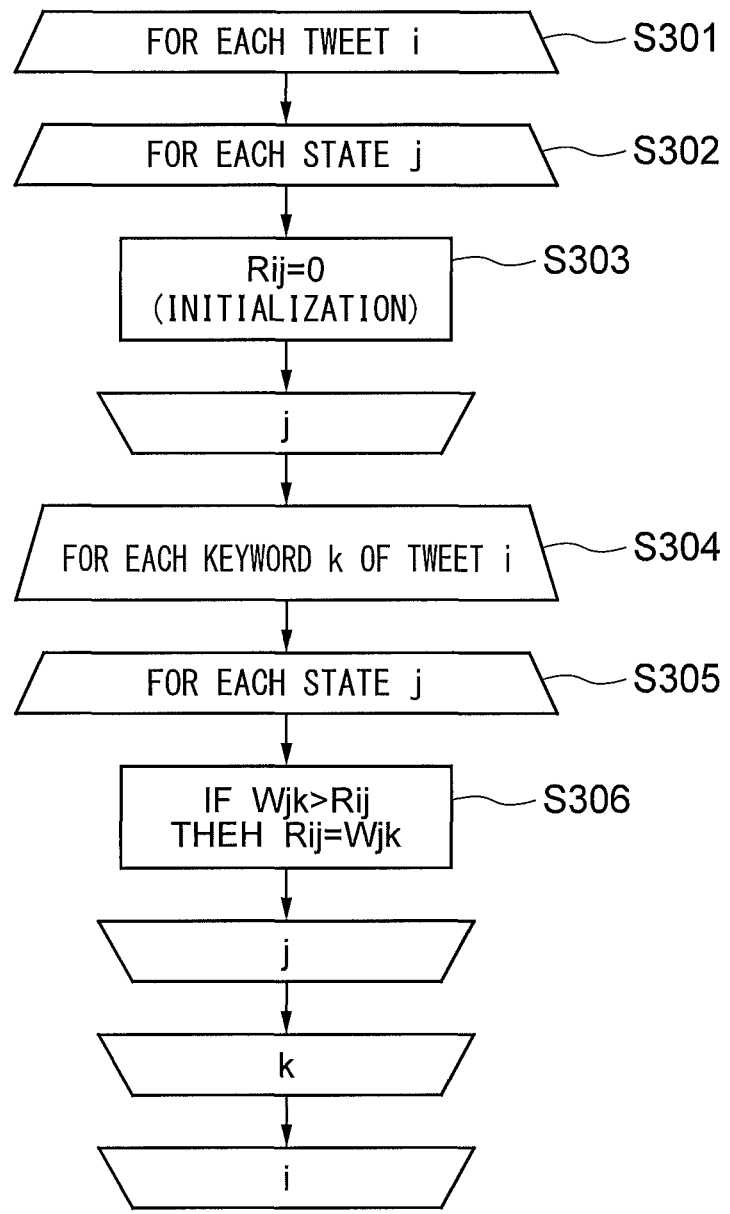
FIG. 14 is a flowchart of the process of identifying, in a case where a plurality of keywords related to a certain state are present, the relevant level of the state.

In the following description, a method for summing up the number of voice tweets by using the relevant level will be shown. First, for each voice tweet, the highest relevant level is identified on a state basis. FIG. 14 is a flowchart of the summing-up method.

For each voice tweet "i" (S301), for each state "j" (S302), "Rij" is initialized to 0 (S303). Steps S301 to S303 belong to an "Rij" initialization phase. Next, for each keyword "k" contained in the voice tweet "i" (S304), "Rij" is calculated (S306) for each state "j" (S305). Specifically, the relevant level of the keyword "k" is read as "Wjk" from the state-keyword correspondence table, and "Wjk" is compared with "Rij". When "Wjk" is greater than "Rij", "Rij" is updated by using "Wjk" ("Rij"="Wjk"). Among the degrees of association of the keywords "k", the greatest relevant level is thus assigned to "Rij". Steps S304 to S306 correspond to an "Rij" calculation phase.

The number of voice tweets can be obtained in the form of the sum of the relevant levels "Rij" of the voice tweets. The thus determined value is particularly called a tweet occurrence level. For example, a voice tweet occurrence level "Vxyz" related to a state "y" of a certain observed target "x" in a certain month "z" is determined by the sum of the relevant levels "Rij" between each voice tweet "i" and each state "y" that occur in the month "z". A formula for calculating the occurrence level "Vxyz" is presented below. The occurrence level can be used instead of the number of voice tweets described above.

$$V_{xyz} = \sum_{i \in \text{tweet that occurs in month } z} R_{iy} \qquad \text{[FORMULA 1]}$$

An example of a method for summing up keywords by using the relevant level will next be shown. The relevant level between a state "j" and a keyword "k" is written as "Wjk". The number of occurrences of keywords related to the state "j" in a certain month "z" is adjusted by using the relevant level. Now, let "nykz" be the number of keywords "k" related to the state "y" of the observed target "x" in the month "z". The number of occurrences of keywords can then be determined as the sum of "nykz" weighted by "Wyk". The thus determined value is particularly called a keyword occurrence level. A formula for calculating a keyword occurrence level "Mxyz" related to the state "y" of the observed target "x" in the month "z" is shown below. The keyword occurrence level can be used instead of the number of occurrences of keywords described above.

$$M_{xyz} = \sum_{k} W_{yk} \times n_{ykz} \qquad \text{[FORMULA 2]}$$

In a variety of pieces of presentation information shown in the first embodiment, the display color of the related keyword contained in information data in each cell can also be changed in accordance with the relevant level. For example, the display color of a keyword is defined by using an RGB specification scheme as (R, G, B)=(255, 255*(1−relevant level), 255*(1−relevant level)). In this definition, a keyword having a greater relevant level (closer to 1) is displayed with higher brightness (deep red, for example), and a keyword having a smaller relevant level (closer to 0) is displayed with lower brightness (pale red, for example). Further, the font size of a keyword can also be increased in accordance with the relevant level. For example, the font size is increased as the relevant level increases. A keyword can thus be displayed in an enhanced manner in accordance with the relevant level.

In the present embodiment described above, the case where the relevant level is defined in relation to the combination of a state and a keyword has been presented. As an extended example, a weight on a profession basis may be defined in addition to the relevant level (or instead of the relevant level) in relation to the combination of a state and a keyword. The importance of a keyword varies in some cases depending on the profession of a user who has tweeted the keyword. In view of the fact described above, a weight on a profession basis is defined in the state-keyword correspondence table, and at the time of summing-up operation using Formula 1 or 2 described above, the sum is further multiplied by the weight determined in accordance with the profession of a user who has tweeted the voice tweet. The weight of the keyword can thus be adjusted in accordance with the attribute of the user who has tweeted the voice tweet.

Fourth Embodiment

In cooperation between home medical treatment and home care, different types of professionals, such as a doctor, a nurse, a pharmacist, and a care giver, observe an observed target on the basis of specialties of the professions, and voice tweets tweeted as results of the observation are registered. The states of interest differ according to the professions.

In view of the fact described above, state-keyword correspondence tables held in the correspondence table storage 12 which differ depending on professions enable each observer to evaluate targets appropriately according to their professions. The profession of an observer may be acquired on the basis of the observer ID from the user master.

Instead of state-keyword correspondence tables on a profession basis, state-keyword correspondence tables on a user basis (observer basis) may be defined and held in the correspondence table storage 12. State-keyword correspondence tables can thus be defined from a viewpoint of an interest of a user-self, and the user can use the tables in the evaluation. Further, state-keyword correspondence tables may be defined on an observed target basis and held in the correspondence table storage 12.

The present information processing apparatus 101 uses the state-keyword correspondence tables on a profession basis, a user basis, and an observed target basis to carry out the processes in the first to third embodiments.

Fifth Embodiment

In the first embodiment, the case where the display color is controlled for each cell of presentation information has been presented. A more general description of the case will be made below.

For a certain observed target "x", in a table having a vertical axis "A" and a horizontal axis "B", let "Mxab" be the number of voice tweets in each cell ("A"="a", "B"="b") and "Kxab" be the number of keywords, and the display of the cell can be controlled as follows:

For example, consider a case of a table having a vertical axis representing states and a horizontal axis representing timeframes and containing voice tweets tweeted within the past 6 months (see FIG. 6). The number of voice tweets about each observed target "u" in association with each state "a" in each timeframe "b" is determined. The number of occurrences of voice tweets related to each state per day is then determined for each observed target, as described with reference to the flowchart in FIG. 10. The determined number is multiplied by 183, whereby the number of occurrences of voice tweets "Nuab" related to the state "a" of each observed target "u" in the timeframe "b" per 6 months can be determined. The same method can be used to determine the number of keywords "Kuab".

The distribution of the number of occurrences of voice tweets or keywords related to the state "x" of all observed targets in the timeframe "y" per 6 months can thus be obtained.

Instead of the distribution for all observed targets, determination of the distribution for observed targets having the same age or age group (age width of 10, for example) of the observed target and determination of other values may be performed as in the second embodiment.

As a result, the same method as in the second embodiment can be used to determine where "Mxab" is located in the distribution "Nuab" of all observed targets "u", that is, how much top percentage (upper percentile value) corresponds to the point where "Mxab" is located in the "Nuab" distribution, and the display color of the cell described above can be changed in accordance with the upper percentile value. Also in a table having a vertical axis representing states and a horizontal axis representing professions (see FIG. 8) and other tables, the number of voice tweets and the number of keywords in a cell can be evaluated by the same calculation.

In a case where the vertical or horizontal axis represents states, evaluation of the number of voice tweets or the number of keywords by using the relevant level can be made, as shown in the third embodiment.

The information processing apparatus of each of the first to fifth embodiments as described above may also be realized using a general-purpose computer device as basic hardware. That is, each function block in the information processing apparatus can be realized by causing a processor mounted in the above general-purpose computer device to execute a program. In this case, the embodiment may be realized by installing the above described program in the computer device beforehand or may be realized by storing the program in a storage medium such as a CD-ROM or distributing the above described program over a network and installing this program in the computer device as appropriate. Furthermore, the database or the storage in the information processing apparatus may also be realized using a memory device or hard disk incorporated in or externally added to the above described computer device or a storage medium such as CD-R, CD-RW, DVD-RAM, DVD-R as appropriate.

The present invention is not limited to the above described embodiments as they are, and constituent elements can be substantiated with deformation within a range not deviating from the gist thereof in a practical phase. Various inventions can be formed by appropriate combinations of the plurality of constituent elements disclosed in the above described embodiments. For example, some constituent elements can be deleted from all the constituent elements shown in the embodiments, and the elements across the different embodiments can be appropriately combined.

EXPLANATION OF SINGS 101 information processing apparatus
102 user terminal
103 network
11 data processor
12 correspondence table storage
13 voice tweet data storage
14 observed target master storage
15 user master storage
16 output device
17 warning device

The invention claimed is:

1. An information processing apparatus comprising:
a first storage to store correspondence data in which a plurality of mental and physical states of a person are related to keywords in a state-keyword correspondence table, wherein the plurality of mental and physical states include at least one of cognition, nutrition, mis-swallowing, or tumble/fall;
a second storage to store messages representing contents tweeted for a care receiver by a plurality of care givers, wherein the messages comprise one or both of voice messages and text messages;
a data processor, wherein the data processor is configured to:
  detect the keywords related to each of the plurality of mental and physical states within the messages based on the correspondence data, the keywords being extracted from the one or both of the voice messages and the text messages using morphological analysis;
  create presentation information to be presented to a user in a screen, wherein the presentation information has a form of a matrix of information data, a first axis of the matrix corresponding to the plurality of mental and physical states and a second axis of the matrix corresponding to predetermined time periods or identities of the care givers, wherein the information data comprises a list of keywords related to each of the plurality of mental and physical states detected within the messages and a text of each of the messages, and wherein the information data is arranged in cells of the matrix based on the relationship of the detected keywords to the plurality of mental and physical states; and
  sum, for each cell of the matrix, one or both of a number of pieces of the information data and a number of detected keywords arranged in the cell; and
a warning device communicatively coupled to the data processor configured to transmit a warning message to a user terminal when the sum associated with at least one cell of the matrix is greater than or equal to a predetermined threshold.

2. The information processing apparatus according to claim 1, wherein the messages in the second storage are related to time information of tweets of the messages, and
the data processor categorizes, for each of the plurality of mental and physical states, the information data based on the time information and arranges the information data according to the categorization to generate the matrix of the information data.

3. The information processing apparatus according to claim 1, wherein the messages in the second storage are related to professions of the care givers who have tweeted the messages, and
the data processor categorizes, for each of the plurality of mental and physical states, the information data according to the professions of the care givers and arranges the information data according to the categorization to generate the matrix of the information data.

4. The information processing apparatus according to claim 1, wherein the data processor categorizes, for each of the plurality of mental and physical states, the information data based on the care givers and arranges the information data according to the categorization to generate the matrix of the information data.

5. The information processing apparatus according to claim 1, wherein the messages stored in the second storage are related to professions of the care givers who have tweeted the messages and time information of tweets of the messages, and
the data processor categorizes the information data in accordance with the professions of the care givers and the time information and arranges the information data according to the categorization to create another presentation information different from the presentation information.

6. The information processing apparatus according to claim 1, further comprising:
an output device configured to transmit the presentation information to a user terminal including a display,
wherein the first storage stores relevant levels representing a magnitude of relevance between each of the plurality of mental and physical states and each of the keywords,
the data processor determines a method of displaying the information data in accordance with the relevant levels of the detected keywords related to each of the plurality of mental and physical states, and
the output device transmits information that identifies the display method determined by the data processor to the user terminal.

7. The information processing apparatus according to claim 1, further comprising:
an output device configured to transmit the presentation information to a user terminal including a display,
wherein the data processor determines a method of displaying information data related to a particular state of the plurality of mental and physical states in accordance with a total number of pieces of the information data related to the state, and
the output device transmits information that identifies the display method determined by the data processor to the user terminal.

8. The information processing apparatus according to claim 1, further comprising:
an output device configured to transmit the presentation information to a user terminal including a display,
wherein the data processor determines a method of displaying information data related to a particular state of the plurality of mental and physical states in accordance with a total number of detected keywords related to the state in the information data, and
the output device transmits information that identifies the display method determined by the data processor to the user terminal.

9. The information processing apparatus according to claim 1, wherein the predetermined time periods are a day basis, a week basis, a month basis, a timeframe basis, an hour basis, or a season unit basis.

10. An information processing method implemented by a computer, the method comprising:
reading correspondence data from a state-keyword correspondence table in which a plurality of mental and physical states of a person are related to keywords, wherein the plurality of mental and physical states include at least one of cognition, nutrition, misswallowing, or tumble/fall;
reading messages representing contents tweeted for a care receiver by a plurality of care givers, wherein the messages comprise one or both of voice messages and text messages;
detecting keywords related to each of the plurality of mental and physical states within the messages based on the correspondence data, the keywords being extracted from the one or both of the voice messages and the text messages using morphological analysis;
creating presentation information to be presented to a user in a screen, wherein the presentation information has a form of a matrix of information data, a first axis of the matrix corresponding to the plurality of mental and physical states and a second axis of the matrix corresponding to predetermined time periods or identities of the care givers, wherein the information data comprises a list of keywords related to each of the plurality of mental and physical states detected within the messages and a text of each of the messages, and wherein the information data is arranged in cells of the matrix based on the relationship of the detected keywords to the plurality of mental and physical states;
summing, for each cell of the matrix, one or both of a number of pieces of information data a number of detected keywords arranged in the cell; and
transmitting a warning message to a user terminal when the sum associated with at least one cell of the matrix is greater than or equal to a predetermined threshold.

11. The information processing method of claim 10, wherein the messages in the second storage are related to time information of tweets of the messages, and further comprising:
categorizing, for each of the plurality of mental and physical states, the information data based on the time information; and
arranging the information data according to the categorization to generate the matrix of the information data.

12. The information processing method of claim 10, wherein the messages in the second storage are related to professions of the care givers who have tweeted the messages, and further comprising:
categorizing, for each of the plurality of mental and physical states, the information data according to the professions of the care givers; and
arranging the information data according to the categorization to generate the matrix of the information data.

13. The information processing method of claim 10, further comprising:
categorizing, for each of the plurality of mental and physical states, the information data based on the care givers; and
arranging the information data according to the categorization to generate the matrix of the information data.

14. The information processing method of claim 10, wherein the messages stored in the second storage are related to professions of the care givers who have tweeted the messages and time information of tweets of the messages, and further comprising:
categorizing the information data in accordance with the professions of the care givers and the time information; and
arranging the information data according to the categorization to create another presentation information different from the presentation information.

15. The information processing method of claim 10, further comprising:
transmitting, via an output device, the presentation information to a user terminal including a display;
storing, in the first storage, relevant levels representing a magnitude of relevance between each of the plurality of mental and physical states and each of the keywords;
determining a method of displaying the information data in accordance with the relevant levels of the detected keywords related to each of the plurality of mental and physical states; and
transmitting, via the output device, information that identifies the display method determined by the data processor to the user terminal.

16. The information processing method of claim 10, further comprising:
transmitting, via an output device, the presentation information to a user terminal including a display;
determining a method of displaying information data related to a particular state of the plurality of mental and physical states in accordance with a total number of pieces of the information data related to the state; and
transmitting, via the output device, information that identifies the display method determined by the data processor to the user terminal.

17. The information processing method of claim 10, further comprising:
transmitting, via an output device, the presentation information to a user terminal including a display;
determining a method of displaying information data related to a particular state of the plurality of mental and physical states in accordance with a total number of detected keywords related to the state in the information data; and
transmitting, via the output device, information that identifies the display method determined by the data processor to the user terminal.

18. A non-transitory computer-readable medium containing program instructions that, when executed by a processor of a computer system, cause the computer system to:
store, in a first storage, correspondence data in which a plurality of mental and physical states of a person are related to keywords in a state-keyword correspondence table, wherein the plurality of mental and physical states include at least one of cognition, nutrition, misswallowing, or tumble/fall;

store, in a second storage, messages representing contents tweeted for a care receiver by a plurality of care givers, wherein the messages comprise one or both of voice messages and text messages;

detect, via a data processor, the keywords related to each of the plurality of mental and physical states within the messages based on the correspondence data, the keywords being extracted from the one or both of the voice messages and the text messages using morphological analysis;

create, via a data processor, presentation information to be presented to a user in a screen, wherein the presentation information has a form of a matrix of information data, a first axis of the matrix corresponding to the plurality of mental and physical states and a second axis of the matrix corresponding to predetermined time periods or identities of the care givers, wherein the information data comprises a list of keywords related to each of the plurality of mental and physical states detected within the messages and a text of each of the messages, and wherein the information data is arranged in cells of the matrix based on the relationship of the detected keywords to the plurality of mental and physical states; and sum, for each cell of the matrix, one or both of a number of pieces of the information data and a number of detected keywords arranged in the cell; and transmit, via a warning device communicatively coupled to the data processor, a warning message to a user terminal when the sum associated with at least one cell of the matrix is greater than or equal to a predetermined threshold.

19. The non-transitory computer-readable medium of claim 18, containing further program instructions that cause the computer system to:

categorize, for each of the plurality of mental and physical states, the information data based on the care givers; and arrange the information data according to the categorization to generate the matrix of the information data.

20. The non-transitory computer-readable medium of claim 18, containing further program instructions that cause the computer system to:

transmit, via an output device, the presentation information to a user terminal including a display;

determine a method of displaying information data related to a particular state of the plurality of mental and physical states in accordance with one or both of 1) a total number of pieces of the information data related to the state, and 2) a total number of detected keywords related to the state in the information data; and transmit, via the output device, information that identifies the display method determined by the data processor to the user terminal.

\* \* \* \* \*

UNITED STATES PATENT AND TRADEMARK OFFICE
CERTIFICATE OF CORRECTION

PATENT NO. : 11,043,287 B2
APPLICATION NO. : 15/120105
DATED : June 22, 2021
INVENTOR(S) : Kentaro Torii et al.

Page 1 of 1

It is certified that error appears in the above-identified patent and that said Letters Patent is hereby corrected as shown below:

In the Claims

At Column 17, Line 50, "information data a" should be -- information data and a --.

At Column 19, Line 25, "states; and" should be -- states; --.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*